US011656221B2

(12) United States Patent
Avery et al.

(10) Patent No.: US 11,656,221 B2
(45) Date of Patent: May 23, 2023

(54) METHODS TO IDENTIFY MODULATORS OF ACTIN-BINDING PROTEINS

(71) Applicant: Regents of the University of Minnesota, Minneapolis, MN (US)

(72) Inventors: Adam William Avery, Rochester Hills, MI (US); Thomas S. Hays, St. Paul, MN (US); David D. Thomas, Minneapolis, MN (US); Michael E. Fealey, Dallas, TX (US); Robyn T. Rebbeck, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 258 days.

(21) Appl. No.: 16/897,977

(22) Filed: Jun. 10, 2020

(65) Prior Publication Data
US 2020/0393445 A1 Dec. 17, 2020

Related U.S. Application Data

(60) Provisional application No. 62/859,864, filed on Jun. 11, 2019.

(51) Int. Cl.
*G01N 21/64* (2006.01)
*G01N 33/50* (2006.01)

(52) U.S. Cl.
CPC ....... *G01N 33/502* (2013.01); *G01N 21/6428* (2013.01); *G01N 2021/6439* (2013.01); *G01N 2333/4712* (2013.01)

(58) Field of Classification Search
CPC ............ G01N 33/502; G01N 21/6428; G01N 2021/6439; G01N 2333/4712;
(Continued)

(56) References Cited

U.S. PATENT DOCUMENTS 6,816,102 B2   11/2004 Pavicic
7,157,566 B2 *  1/2007 Tsien ................... G01N 33/84
                                                            435/69.7

(Continued)

FOREIGN PATENT DOCUMENTS

CN   108267435 A   7/2018
EP     2294159 B1   9/2012
(Continued)

OTHER PUBLICATIONS

Guhathakurta et al.,High-throughput screen, using time-resolved FRET, yields actinbinding compounds that modulate actin-myosin structure and function, JBC Papers in Press, 2018, 1-21 (Year: 2018).*

(Continued)

*Primary Examiner* — David P Porta
*Assistant Examiner* — Djura Malevic
(74) *Attorney, Agent, or Firm* — Mueting Raasch Group

(57) ABSTRACT

The present disclosure provides methods for identifying compounds that cause structural changes in a protein bound to an actin filament. The methods include the use of cells that include two actin-binding proteins, each labeled with a chromophore, and exposing the cells to a test compound. The method further includes detecting a change in fluorescence resonance energy transfer (FRET) between the chromophores.

20 Claims, 12 Drawing Sheets

(58) Field of Classification Search
CPC ......... G01N 33/542; G01N 2021/6441; G01N 2500/02; G01N 21/6408
See application file for complete search history.

(56) References Cited

U.S. PATENT DOCUMENTS

| | | | |
|---|---|---|---|
| 7,413,862 | B2 | 8/2008 | Van Dongen et al. |
| 7,674,584 | B2* | 3/2010 | Briggs ................. G01N 33/542 435/7.1 |
| 7,888,090 | B2* | 2/2011 | Barnikow ................ C12N 9/10 435/71.1 |
| 8,957,029 | B2* | 2/2015 | Wedlich-Soldner ....................... C07K 14/395 536/26.6 |
| 9,255,128 | B2* | 2/2016 | Wedlich-Soldner ....................... C07K 14/43595 |
| 9,693,954 | B2* | 7/2017 | Mooney ................ A61K 31/454 |
| 10,794,898 | B2* | 10/2020 | Thomas ............. G01N 21/6408 |
| 11,345,964 | B2* | 5/2022 | Albitar ................. C12Q 1/6816 |
| 11,360,096 | B2* | 6/2022 | Pack ................... G01N 33/6809 |
| 2003/0059835 | A1* | 3/2003 | Tsien ............... C07K 14/43504 435/7.1 |
| 2004/0023874 | A1* | 2/2004 | Burgess ................. C07K 14/47 435/7.1 |
| 2006/0003420 | A1* | 1/2006 | Tsien ....................... C12Q 1/25 435/325 |
| 2006/0068414 | A1* | 3/2006 | Kennedy .............. C12Q 1/6888 435/6.1 |
| 2006/0094101 | A1* | 5/2006 | Yannoni .................. A61P 11/00 435/7.1 |
| 2006/0134644 | A1 | 6/2006 | Hartel et al. |
| 2007/0207532 | A1* | 9/2007 | Barnikov ................ C12N 9/10 435/183 |
| 2008/0064054 | A1* | 3/2008 | Fernandez-Salas ......................... C07K 14/435 536/23.7 |
| 2011/0126305 | A1* | 5/2011 | Chang .................... C07K 14/28 435/254.2 |
| 2011/0165593 | A1* | 7/2011 | Barnikow ................ C12N 9/10 435/193 |
| 2012/0021926 | A1 | 1/2012 | Thomas et al. |
| 2013/0231262 | A1 | 9/2013 | Robia |
| 2013/0272966 | A1* | 10/2013 | Xiong ................... C12N 9/0069 435/7.1 |
| 2014/0039156 | A1* | 2/2014 | Lasmezas .......... A61K 31/4745 506/9 |
| 2015/0020487 | A1 | 1/2015 | Scott et al. |
| 2015/0113671 | A1* | 4/2015 | Wedlich-Soldner ......................... G01N 33/502 435/348 |
| 2015/0204847 | A1* | 7/2015 | Thomas ............. G01N 21/6408 435/29 |
| 2015/0309054 | A1 | 10/2015 | Diamond et al. |
| 2015/0369740 | A1* | 12/2015 | Cohen ................. C07K 14/705 536/23.5 |
| 2018/0238901 | A1* | 8/2018 | Schaaf ................ G01N 33/542 |
| 2019/0353663 | A9* | 11/2019 | Schaaf ................ G01N 33/582 |
| 2020/0264162 | A1* | 8/2020 | Sachs ................. G01N 33/542 |
| 2020/0393445 | A1* | 12/2020 | Avery ................. G01N 33/542 |
| 2021/0255195 | A1* | 8/2021 | Schaaf ............... G01N 33/6845 |

FOREIGN PATENT DOCUMENTS

| | | |
|---|---|---|
| EP | 3055675 A1 | 8/2016 |
| WO | WO 2009/156019 A1 | 12/2009 |
| WO | 2010085514 | 7/2010 |
| WO | WO 2015/052331 A1 | 4/2015 |

OTHER PUBLICATIONS

Sanabria et al., Spatial regulation of the actin cytoskeleton by HSF-1 during aging, Molecular Biology of the Cell, vol. 29,Oct. 15, 2018 pp. 2522-2527 (Year: 2018).*

Martin et al., Accepting from the best donor; analysis of long-lifetime donor fluorescent protein pairings to optimise dynamic FLIM-based FRET experiments, Plos One (Year: 2018).*

Avery et al., Structural basis for high-affinity actin binding revealed by a β-III-spectrin SCA5 missense mutation, Nature Communications, 8:1350, pp. 1-8 (Year: 2018).*

Akrap et al., Forster distances for fluorescence resonant energy transfer between mCherry and other visible fluorescent proteins. *Anal Biochem* 402, 105-106 (2010).

Amin et al., Oncogene Overdose: Too Much of a Bad Thing for Oncogene-Addicted Cancer Cells. *Biomark Cancer* 7, 25-32 (2015).

Asakura et al., Isolation and characterization of a novel actin filament-binding protein from *Saccharomyces cerevisiae*. *Oncogene* 16, 121-130 (1998).

Avery et al., A human beta-III-spectrin spinocerebellar ataxia type 5 mutation causes high-affinity F-actin binding, *Sci Rep* 6, 21375 (2016).

Avery et al., Structural basis for high-affinity actin binding revealed by a beta-III-spectrin SCA5 missense mutation, *Nat Commun* 8, 1350 (2017).

Avery et al., beta-III-spectrin spinocerebellar ataxia type 5 mutation reveals a dominant cytoskeletal mechanism that underlies dendritic arborization. *Proc Natl Acad Sci U S A* 114, E9376-E9385 (2017).

Babaoglu et al., Comprehensive mechanistic analysis of hits from high-throughput and docking screens against beta-lactamase. *J Med Chem* 51, 2502-2511 (2008).

Banuelos et al., Structural comparisons of calponin homology domains: implications for actin binding. *Structure* 6, 1419-1431 (1998).

Bubb et al., Swinholide A is a microfilament disrupting marine toxin that stabilizes actin dimers and severs actin filaments. *J Biol Chem* 270, 3463-3466 (1995).

Burk et al., Spinocerebellar ataxia type 5: clinical and molecular genetic features of a German kindred. *Neurology* 62, 327-329 (2004).

Cho et al., A family with spinocerebellar ataxia type 5 found to have a novel missense mutation within a SPTBN2 spectrin repeat. *Cerebellum* 12, 162-164 (2013).

Clark et al., Skeletal dysplasias due to filamin A mutations result from a gain-of-function mechanism distinct from allelic neurological disorders. *Hum Mol Genet* 18, 4791-4800 (2009).

Clarkson et al., Beta-III spectrin mutation L253P associated with spinocerebellar ataxia type 5 interferes with binding to Arp1 and protein trafficking from the Golgi. *Hum Mol Genet* 19, 3634-3641 (2010).

Cooper et al., Microinjection of gelsolin into living cells. *J Cell Biol* 104, 491-501 (1987).

Cornea et al., High-throughput FRET assay yields allosteric SERCA activators. *J Biomol Screen* 18, 97-107 (2013).

Courtemanche et al., Avoiding artefacts when counting polymerized actin in live cells with LifeAct fused to fluorescent proteins. *Nat Cell Biol* 18, 676-683 (2016).

Dahlin et al., Pains in the assay: chemical mechanisms of assay interference and promiscuous enzymatic inhibition observed during a sulfhydryl-scavenging HTS. *J Med Chem* 58, 2091-2113 (2015).

Dahlin et al., The essential roles of chemistry in high-throughput screening triage. *Future Med Chem* 6, 1265-1290 (2014).

Doak et al., Colloid formation by drugs in simulated intestinal fluid. *J Med Chem* 53, 4259-4265 (2010).

Duff et al., Mutations in the N-terminal actin-binding domain of filamin C cause a distal myopathy. *Am J Hum Genet* 88, 729-740 (2011).

Ferreira et al., Complementarity between a docking and a high-throughput screen in discovering new cruzain inhibitors. *J Med Chem* 53, 4891-4905 (2010).

Gao et al., beta-III spectrin is critical for development of purkinje cell dendritic tree and spine morphogenesis. *J Neurosci* 31, 16581-16590 (2011).

Girolami et al., Novel α-actinin 2 variant associated with familial hypertrophic cardiomyopathy and juvenile atrial arrhythmias: a massively parallel sequencing study. Circ Cardiovasc Genet 7, 741-750 (2014).

(56) References Cited

OTHER PUBLICATIONS

Gruber et al., Discovery of enzyme modulators via high-throughput time-resolved FRET in living cells. *J Biomol Screen* 19, 215-222 (2014).
Guhathakurta et al., High-throughput screen, using time-resolved FRET, yields actin-binding compounds that modulate actin-myosin structure and function. *J Biol Chem* 293, 12288-12298 (2018).
Harris et al., Steric regulation of tandem calponin homology domain actin-binding affinity. *Mol Biol Cell* 30, 3112-3122 (2019).
Henderson et al., Disease-causing missense mutations in actin binding domain 1 of dystrophin induce thermodynamic instability and protein aggregation. *Proc Natl Acad Sci U S A* 107, 9632-9637 (2010).
Holmes et al., Electron cryo-microscopy shows how strong binding of myosin to actin releases nucleotide. *Nature* 425, 423-427 (2003).
Hughes et al., Principles of early drug discovery. *Br J Pharmacol* 162, 1239-1249 (2011).
Hurley et al., Non-pungent long chain capsaicin-analogs arvanil and olvanil display better anti-invasive activity than capsaicin in human small cell lung cancers. *Cell Adh Migr* 11, 80-97 (2017).
Ikeda et al., Spectrin mutations cause spinocerebellar ataxia type 5. *Nat Genet* 38, 184-190 (2006).
Irwin et al., An Aggregation Advisor for Ligand Discovery. *J Med Chem* 58, 7076-7087 (2015).
Iwamoto et al., Structural basis of the filamin A actin-binding domain interaction with F-actin. *Nat Struct Mol Biol* 25, 918-927 (2018).
Jacob et al., Case of infantile onset spinocerebellar ataxia type 5. *J Child Neurol* 28, 1292-1295 (2012).
Jager et al., High level transient production of recombinant antibodies and antibody fusion proteins in HEK293 cells. *BMC Biotechnol* 13, 52 (2013).
Kaplan et al., Mutations in ACTN4, encoding alpha-actinin-4, cause familial focal segmental glomerulosclerosis. *Nat Genet* 24, 251-256 (2000).
Kumar et al., Cardiotoxicity of calmidazolium chloride is attributed to calcium aggravation, oxidative and nitrosative stress, and apoptosis. *Free Radic Biol Med* 47, 699-709 (2009).
Liu et al., A Novel Missense Mutation in the Spectrin Beta Nonerythrocytic 2 Gene Likely Associated with Spinocerebellar Ataxia Type 5. *Chin Med J (Engl)* 129, 2516-2517 (2016).
Lo et al., Targeting the ensemble of heterogeneous tau oligomers in cells: A novel small molecule screening platform for tauopathies. *Alzheimers Dement* 15, 1489-1502 (2019).
Lo et al., Noncompetitive inhibitors of TNFR1 probe conformational activation states. *Sci Signal* 12, eaav5637 (2019).
Lo et al., An Innovative High-Throughput Screening Approach for Discovery of Small Molecules That Inhibit TNF Receptors. *SLAS Discov* 22, 950-961 (2017).
Loignon et al., Stable high volumetric production of glycosylated human recombinant IFNalpha2b in HEK293 cells. *BMC Biotechnol* 8, 65 (2008).
Lopata et al., Affimer proteins for F-actin: novel affinity reagents that label F-actin in live and fixed cells. *Sci Rep* 8, 6572 (2018).
Mizuno et al., Infantile-onset spinocerebellar ataxia type 5 associated with a novel SPTBN2 mutation: A case report. *Brain Dev* 41, 630-633 (2019).
Muretta et al., High-performance time-resolved fluorescence by direct waveform recording. *Rev Sci Instrum* 81, 103101 (2010).
Murphy et al., Congenital macrothrombocytopenia-linked mutations in the actin-binding domain of alpha-actinin-1 enhance F-actin association. *FEBS Lett* 590, 685-695 (2016).
Ni et al., Discovery of candesartan cilexetic as a novel neddylation inhibitor for suppressing tumor growth. *Eur J Med Chem* 185, 111848 (2020).
Nicita et al., Heterozygous missense variants of SPTBN2 are a frequent cause of congenital cerebellar ataxia. *Clin Genet* 96, 169-175 (2019).

Ohara et al., Characterization of a new beta-spectrin gene which is predominantly expressed in brain. *Brain Res Mol Brain Res* 57, 181-192 (1998).
Perkins et al., Loss of beta-III spectrin leads to Purkinje cell dysfunction recapitulating the behavior and neuropathology of spinocerebellar ataxia type 5 in humans. *J Neurosci* 30, 4857-4867 (2010).
Peterson et al. Fluorescence lifetime plate reader: resolution and precision meet high-throughput. *Rev Sci Instrum* 85, 113101 (2014).
Prochniewicz et al., Cooperativity in F-actin: chemical modifications of actin monomers affect the functional interactions of myosin with unmodified monomers in the same actin filament. *Biophys J* 65, 113-123 (1993).
Prochniewicz et al., Myosin isoform determines the conformational dynamics and cooperativity of actin filaments in the strongly bound actomyosin complex. *J Mol Biol* 396, 501-509 (2010).
Prochniewicz et al., Structural dynamics of actin during active interaction with myosin: different effects of weakly and strongly bound myosin heads. *Biochemistry* 43, 10642-10652 (2004).
Prochniewicz et al., Microsecond rotational dynamics of actin: spectroscopic detection and theoretical simulation, *J Mol Biol* 255, 446-457 (1996).
Rebbeck et al., High-Throughput Screens to Discover Small-Molecule Modulators of Ryanodine Receptor Calcium Release Channels. *SLAS Discov* 22, 176-186 (2017).
Rebbeck et al., RyR1-targeted drug discovery pipeline integrating FRET-based high-throughput screening and human myofiber dynamic Ca(2+) assays. *Sci Rep* 10, 1791 (2020).
Riedl et al., Lifeact: a versatile marker to visualize F-actin. *Nat Methods* 5, 605-607 (2008).
Sawyer et al., Disease-associated substitutions in the filamin B actin binding domain confer enhanced actin binding affinity in the absence of major structural disturbance: Insights from the crystal structures of filamin B actin binding domains. *J Mol Biol* 390, 1030-1047 (2009).
Schaaf et al., High-Throughput Spectral and Lifetime-Based FRET Screening in Living Cells to Identify Small-Molecule Effectors of SERCA. *SLAS Discov* 22, 262-273 (2017).
Schaaf et al., Spectral Unmixing Plate Reader: High-Throughput, High-Precision FRET Assays in Living Cells. *SLAS Discov* 22, 250-261 (2017).
Schaaf et al., Red-Shifted FRET Biosensors for High-Throughput Fluorescence Lifetime Screening. *Biosensors (Basel)* 8, 99 (2018).
Shelley et al., Structure-activity studies on gossypol in tumor cell lines. *Anticancer Drugs* 11, 209-216 (2000).
Shyu et al., Visualization of ternary complexes in living cells by using a BiFC-based FRET assay. *Nat Protoc* 3, 1693-1702 (2008).
Singh et al., The N-terminal flanking region modulates the actin binding affinity of the utrophin tandem calponin-homology domain. *Biochemistry* 56, 2627-2636 (2017).
Spector et al., Latrunculins—novel marine macrolides that disrupt microfilament organization and affect cell growth: I. Comparison with cytochalasin D. *Cell Motil Cytoskeleton* 13, 127-144 (1989).
Sorensen et al., Screening of protein kinase inhibitors identifies PKC inhibitors as inhibitors of osteoclastic acid secretion and bone resorption. *BMC Musculoskelet Disord* 11, 250 (2010).
Stankewich et al., Targeted deletion of betaIII spectrin impairs synaptogenesis and generates ataxic and seizure phenotypes. *Proc Natl Acad Sci U S A* 107, 6022-6027 (2010).
Stroik et al., Targeting protein-protein interactions for therapeutic discovery via FRET-based high-throughput screening in living cells. *Sci Rep* 8, 12560 (2018).
Terry et al., Misakinolide A is a marine macrolide that caps but does not sever filamentous actin, *J Biol Chem* 272, 7841-7845 (1997).
Wager et al., Defining desirable central nervous system drug space through the alignment of molecular properties, in vitro ADME, and safety attributes. *ACS Chem Neurosci* 1, 420-434 (2010).
Wager et al., Moving beyond rules: the development of a central nervous system multiparameter optimization (CNS MPO) approach to enable alignment of druglike properties. *ACS Chem Neurosci* 1, 435-449 (2010).

(56) References Cited

OTHER PUBLICATIONS

Wang et al., A Japanese SCA5 family with a novel three-nucleotide in-frame deletion mutation in the SPTBN2 gene: a clinical and genetic study. *J Hum Genet* 59, 569-573 (2014).
Weins et al., Mutational and Biological Analysis of alpha-actinin-4 in focal segmental glomerulosclerosis. *J Am Soc Nephrol* 16, 3694-3701 (2005).
Weins et al. Disease-associated mutant, alpha-actinin-4 reveals a mechanism for regulating its F-actin-binding affinity. *Proc Natl Acad Sci USA* 104, 16080-5 (2007).
Zadran et al., Fluorescence resonance energy transfer (FRET)-based biosensors: visualizing cellular dynamics and bioenergetics. *Appl Microbiol Biotechnol* 96, 895-902 (2012).
Holmes et al., "Proteopathic tau seeding predicts tauopathy in vivo" PNAS Plus, Sep. 26, 2014; E4376-E4385.
Acker et al., Considerations for the design and reporting of enzyme assays in high-throughput screening applications, Perspect Sci, May 2014;1(1-6):56-73.
Ai et al., Ca2+/calmodulin-dependent protein kinase modulates cardiac ryanodine receptor phosphorylation and sarcoplasmic reticulum Ca2+ leak in heart failure, CircRes, 2005;97:1314-1322.
Akoury et al., Inhibition of tau filament formation by conformational modulation. J Am Chem Soc 135, 2853-2862 (2013).
Alonso et al., Promotion of hyperphosphorylation by frontotemporal dementia tau mutations, J. Biol. Chem. 2004, 279(33):34873-81.
Andersson et al., Leaky ryanodine receptors in beta-sarcoglycan deficient mice: A potential common defect in muscular dystrophy, Skelet Muscle, 2012;2:9.
Aracena et al., Effects of S-Glutathionylation and S-Nitrosylation on Calmodulin Binding to Triads and FKBP12 Binding to Type 1 Calcium Release Channels, Antioxid Redox Signal, 2005;7:870-881.
Arbabian et al., Endoplasmic reticulum calcium pumps and cancer, Biofactors, 2011;37:139-149.
Ariazi et al., Estrogen-related receptors as emerging targets in cancer and metabolic disorders Curr Top Med Chem, 2006;6:203-215.
Arnou et al., The Plasmodium falciparum Ca(2+)-ATPase PfATP6: insensitive to artemisinin, but a potential drug target, Biochem Soc Trans, 2011;39:823-831.
Ausuebel, R.M., Current Protocols in Molecular Biology, 1994.
Avila et al., Role of tau protein in both physiological and pathological conditions. Physiol Rev 84, 361-384 (2004).
Baggett et al., The Rational Discovery of a Tau Aggregation Inhibitor. Biochemistry 57, 6099-6107 (2018).
Bagshaw et al., ATP analogues at a glance, J Cell Science, Feb. 1, 2001;114(3):459-460.
Ballatore et al., Tau-mediated neurodegeneration in Alzheimer's disease and related disorders. Nat Rev Neurosci 8, 663-672 (2007).
Balog et al., AmJPhysiolHeartCircPhysiol., 2006;290:H794-H799.
Balshaw et al., Calmodulin Binding and Inhibition of Cardiac Muscle Calcium Release Channel (Ryanodine Receptor), JBiolChem, 2001;276;20144-20153.
Balshaw et al., Modulation of intracellular calcium-release channels by calmodulin, J Membr Biol., 2002;185:1-8.
Banerjee et al., Proteoliposome as the model for the study of membrane-bound enzymes and transport proteins, Molecular and Cellular Biochemistry, 1983;50:3-15.
Beechem et al., Numer Comput Methods, 1992;210;37.
Berger et al., Accumulation of pathological tau species and memory loss in a conditional model of tauopathy. J Neurosci 27, 3650-3662 (2007).
Bers, Cardiac excitation-contraction coupling, Nature, 2002;415:198-205.
Bers, Cardiac Sarcoplasmic Reticulum Calcium Leak: Basis and Roles in Cardiac Dysfunction, AnnuRevPhysiol, Feb. 2014;76:107-127.
Bers et al., Ratio of ryanodine to dihydropyridine receptors in cardiac and skeletal muscle implications for E-C coupling, Am J Physiol, 1993;264:C1587-C1593.
Bers, Macromolecular complexes regulating cardiac ryanodine receptor function, JMolCellCardiol, 2004;37:417-429.
Bers, Ryanodine receptor S2808 phosphorylation in heart failure: smoking gun or red herring, CircRes, 2012;110:796-799.
Birmingham et al., Statistical methods for analysis of high-throughput RNA interference screens. Nat Methods 6, 569-575 (2009).
Boraso et al., AmJPhysiol., 1994;267:H1010-1016.
Bossuyt et al., Spatiotemporally Distinct Protein Kinase D Activation in Adult Cardiomyocytes in Response to Phenylephrine and Endothelin, J Biol Chem, Sep. 23, 2011;286(38):33390-33400.
Bramblett et al., Abnormal tau phosphorylation at Ser396 in Alzheimer's disease recapitulates development and contributes to reduced microtubule binding. Neuron 10, 1089-1099 (1993).
Breuzard et al., Molecular mechanisms of Tau binding to microtubules and its role in microtubule dynamics in live cells. J Cell Sci 126, 2810-2819 (2013).
Brunden et al., Advances in tau-focused drug discovery for Alzheimer's disease and related tauopathies. Nat Rev Drug Discov 8, 783-793 (2009).
Bubber et al., Mitochondrial abnormalities in Alzheimer brain: mechanistic implications. Ann Neurol 57, 695-703 (2005).
Chen et al., Fluorescence Self-Quenching from Reporter Dyes Informs on the Structural Properties of Amyloid Clusters Formed in Vitro and in Cells. Nano Lett 17, 143-149 (2017).
Chirita et al., Triggers of full-length tau aggregation: a role for partially folded intermediates. Biochemistry 44, 5862-5872 (2005).
Chu et al., The influence of 5-lipoxygenase on Alzheimer's disease-related tau pathology: in vivo and in vitro evidence. Biol Psychiatry 74, 321-328 (2013).
Chun et al., Activation of glycogen synthase kinase 3beta promotes the intermolecular association of tau. The use of fluorescence resonance energy transfer microscopy. J Biol Chem 282, 23410-23417 (2007).
Combs et al., Pseudohyperphosphorylation has differential effects on polymerization and function of tau isoforms. Biochemistry 50, 9446-9456 (2011).
Comley, Fluorescence Lifetime—finally picking up momentum! Drug Discovery World Summer 2010; pp. 71-82.
Cornea et al., Mapping the ryanodine receptor FK506-binding protein subunit using fluorescence resonance energy transfer, J BiolChem, 2010;285:19219-19226.
Cornea et al., FRET-based mapping of calmodulin bound to the RyR1 Ca2+ release channel, PNAS USA, 2009;106:6128-6133.
Cowan et al., Are tau aggregates toxic or protective in tauopathies? Front Neurol 4, 114(2013).
Cowan et al., What is the pathological significance of tau oligomers? Biochem Soc Trans 40, 693-697 (2012).
Cummings et al., Alzheimer's disease drug development pipeline: 2018. Alzheimers Dement (N Y) 4, 195-214 (2018).
De Calignon et al., Caspase activation precedes and leads to tangles. Nature 464, 1201-1204 (2010).
Degorce et al., HTRF: A Technology Tailored for Drug Discovery—A Review of Theoretical Aspects and Recent Applications, Curr Chem Genomics, Mar. 2009;3:22-32.
Devi et al., Heterogeneity of Alzheimer's disease: consequence for drug trials? Alzheimers Res Ther 10, 122 (2018).
Di Primio et al., The Distance between N and C Termini of Tau and of FTDP-17 Mutants is Modulated by Microtubule Interactions in Living Cells. Frontiers in Molecular Neuroscience 10, (2017). https://www.ncbi.nlm.nih.gov/pmc/articles/PMC5492851.
Diaz-Sylvester et al., Halothane modulation of skeletal muscle ryanodine receptors: dependence on Ca2+, Mg2+, and ATP, AmJPhysiolCellPhysiol., Apr. 1, 2008;294(4):C1103-C1112.
Dong et al., Time-resolved FRET reveals the structural mechanism of SERCA-PLB regulation, Biochem Biophys Res Commun, Jun. 27, 2014;449(2):196-201.
Donoso et al., Stimulation of NOX2 in isolated hearts reversibly sensitizes RyR2 channels to activation by cytoplasmic calcium,JMolCellCardiol, Mar. 2014;68:38-46.
Dujardin et al., Different tau species lead to heterogeneous tau pathology propagation and misfolding. Acta Neuropathol Commun 6, 132 (2018).

(56) References Cited

OTHER PUBLICATIONS

Ebneth et al., Overexpression of tau protein inhibits kinesin-dependent trafficking of vesicles, mitochondria, and endoplasmic reticulum: implications for Alzheimer's disease. J Cell Biol 143, 777-794 (1998).
Elbaum-Garfinkle et al., Identification of an aggregation-prone structure of tau. J Am Chem Soc 134, 16607-16613 (2012).
Erickson et al., A Dynamic Pathway for Calcium-Independent Activation of CaMKII by Methionine Oxidation,Cell, May 2, 2008;133:462-474.
Erickson et al., Diabetic hyperglycaemia activates CaMKII and arrhythmias by O-linked glycosylation, Nature, Oct. 17, 2013;502:372-376.
Feher et al., Determinants of calcium loading at steady state in sarcoplasmic reticulum, Biochem Biophys Acta, 1983;727:389-402.
Flach et al., Tau oligomers impair artificial membrane integrity and cellular viability. J Biol Chem 287, 43223-43233 (2012).
Fluorescence Innovations, NovaFluor PR Fluorescence Lifetime Plate Reader Poster, Mar. 2011.
Fluorescence Innovations, Inc., Lifetime Characterization of Cerulean:: Venus FRET Standards in Live Cells Using the NovaFluor PR Fluorescence Lifetime Plate Reader, Poster Presentation, available online, 2 pages (2010).
Fruen et al., Differential Ca2+ sensitivity of skeletal and cardiac muscle ryanodine receptors in the presence of calmodulin, Am J Physiol-Cell Phys, Sep. 1, 2000;279:C724-C733.
Fu et al., Aberrant lipid metabolism disrupts calcium homeostasis causing liver endoplasmic reticulum stress in obesity, Nature, 2011;473:528-531.
Fukuda et al., Enhanced binding of calmodulin to RyR2 corrects arrhythmogenic channel disorder in CPVT-associated myocytes, BiochemBiophysResComm, 2014;448:1-7.
Gakamsky et al., Use of fluorescence lifetime technology to provide efficient protection from false hits in screening applications, Anal. Biochem, Feb. 1, 2011;409(1):89-97.
Gauthier et al., Efficacy and safety of tau-aggregation inhibitor therapy in patients with mild or moderate Alzheimer's disease: a randomised, controlled, double-blind, parallel-arm, phase 3 trial. Lancet 388, 2873-2884 (2016).
Gehrig et al., Hsp72 preserves muscle function and slows progression of sever muscular dystrophy, Nature, 2012;484:394-398.
Gendron et al., The role of tau in neurodegeneration. Mol Neurodegener 4, 13 (2009).
George, Ryanodine Receptor Regulation by Intramolecular Interaction between Cytoplasmic and Transmembrane Domains Jun. 2004 Molecular Biology of the Cell, 15:2627-2638.
Gerson et al., Advances in therapeutics for neurodegenerative tauopathies: moving toward the specific targeting of the most toxic *tau* species. ACS Chem Neurosci 5, 752-769 (2014).
Gerson et al., Potential mechanisms and implications for the formation of tau oligomeric strains. Crit Rev Biochem Mol Biol 51, 482-496 (2016).
Ghetti et al., Invited review: Frontotemporal dementia caused by microtubule-associated protein tau gene (MAPT) mutations: a chameleon for neuropathology and neuroimaging. Neuropathol Appl Neurobiol 41, 24-46 (2015).
Giacobini et al., Alzheimer disease therapy—moving from amyloid-beta to tau. Nat Rev Neurol 9, 677-686 (2013).
Goonasekera et al., Mitigation of muscular dystrophy in mice by SERCA overexpression in skeletal muscle, J Clin Invest, 2011;121:1044-1052.
Gotz et al., What Renders TAU Toxic. Front Neurol 4, 72 (2013).
Grashoff et al., Nature(London), 2010;466:263.
Greensmith et al., The effects of hydrogen peroxide on intracellular calcium handling and contractility in the rat ventricular myocyte, CellCalcium, 2010;48:341-351.
Gribbon et al., Fluorescence readouts in HTS: no gain without pain? Drug Discov Today, Nov. 15, 2003;8(22):1035-1043.
Gruber et al., Phospholamban mutants compete with wild tye for SERCA binding in living cells, Biochem Biophys Res Commun, 2012;420:236-240.
Gruber—In-cell FRET as a Tool to Develop SERCA Activators for Drug or Gene Therapy, Poster presented at 57th Biophysical Society Annual Meeting, Feb. 2-6, 2013; Philadelphia, PA.
Guo et al., Ca2+/Calmodulin-dependent protein kinase II phosphorylation of ryanodine receptor does affect calcium sparks in mouse ventricular myocytes, CircRes, Aug. 18, 2006;99(4):398-406.
Guo et al., FRET detection of calmodulin binding to the RyR2 calcium release channel, BiophysJ, 2011;101:2170-2177.
Guo et al., Kinetics of FKBP12.6 binding to ryanodine receptors in permeabilized cardiac myocytes and effects on Ca sparks, CircRes, Jun. 11, 2010; 106(11):1743-1752.
Guzman-Martinez et al., Tau oligomers as potential targets for Alzheimer's diagnosis and novel drugs. Front Neurol 4, 167 (2013).
Hamilton, SL., Ryanodine receptor structure: Progress and challenges, J Biol Chem, Feb. 13, 2009; 284(7):4047-4051.
Hartigan et al., Tracking HTS Assay Development Time: opportunity for improving drug discovery, Drug Discovery World Summer 2010; pp. 51-58.
Hermanson et al., Dual mechanisms of sHA 14-1 in inducing cell death through endoplasmic reticulum and mitochondria, Mol Pharmacol, 200+9;76:667-678.
Ho et al., JPhysiol., 2011;19:4697-4708.
Hou et al., 2-Color calcium pump reveals closure of the cytoplasmic headpiece with calcium binding, PLoSONE, Jul. 11, 2012;7(7):e40369: 10 pgs.
Houser et al., Protein Kinase A—Mediated Hyperphosphorylation of the Ryanodine Receptor at Serine 2808 Does Not Alter Cardiac Contractility or Cause Heart Failure and Arrhythmias, CircRes, Apr. 11, 2014; 114(8):1320-1327.
Huang et al., Two potential calmodulin-binding sequences in the ryanodine receptor contribute to a mobile, intra-subunit calmodulin-binding domain, J Cell Sci, Oct. 1, 2013;126(19):4527-4535.
Huang et al., Probing Conformational Dynamics of Tau Protein by Hydrogen/Deuterium Exchange Mass Spectrometry. J Am Soc Mass Spectrom 29, 174-182 (2018).
Hubscher et al., Generation of transgenic mice expressing FRET biosensors. Methods Mol Biol 1294, 117-129 (2015).
Hwang et al., Divergent Regulation of Ryanodine Receptor 2 Calcium Release Channels by Arrhythmogenic Human Calmodulin Missense Mutants, CircRes, Mar. 28, 2014; 114(7):1114-1124.
Ikemoto, Regulation of calcium release by interdomain interaction within ryanodine receptors, FrontBiosci, 2002;7:d671-d683.
Ikemoto, Ryanodine Receptors: Structure, Function and Dysfunction in Clinical Diseases, New York, NY; Springer, 2004;53-65.
Inesi et al., Concerted conformational effects of Ca2+ and ATP are required for activation of sequential reactions in the Ca2+ ATPase (SERCA) catalytic cycle, Biochemistry, 2006;45:13769-13778.
Inesi et al., The Ca2+ ATPase of ccardiac sarcoplasmic reticulum: Physiological role and relevance to diseases, Biochem Biophys Res Commun, 2008;369:182-187.
Inglese et al., Nat Chem Biol, 2007;3:466.
Iqbal et al., Hyperphosphorylation-induced tau oligomers. Front Neurol 4, 112 (2013).
Isenberg et al., Biophys J, 1969;9:1337.
Jameson et al., Investigations of protein-protein interactions using time-resolved fluorescence and phasors, Methods, Mar. 1, 2013;59(3):278-286.
Jeganathan et al., Global hairpin folding of tau in solution. Biochemistry 45, 2283-2293 (2006).
Jessup et al., Calcium Upregulation by percutaneous Administration of Gene Therapy in Cardiac Disease (CUPID): a phase 2 trial of intracoronary gene therapy of sarcoplasmic reticulum Ca2+-ATPase in patients with advanced heart failure, Circulation, 2011;124:304-313.
Johnson et al., Cardiac sarcoplasimic reticulum function and regulation of contractility—Introduction, Ann NY Acad Sci, 1998;853:xi-xvi.

(56) References Cited

OTHER PUBLICATIONS

Johnson et al., Pharmacology of the cardiac sarcoplasmic reticulum calcium ATPase phospholamban interaction, Ann NY Acad Sci, 1998;853:380-392.
Jung et al., EMBOMolMed, 2012;4:180-191.
Kadavath et al., Tau stabilizes microtubules by binding at the interface between tubulin heterodimers. Proc Natl Acad Sci U S A 112, 7501-7506 (2015).
Kast et al., Proc Natl Acad Sci USA, 2010; 107:8207.
Kfoury et al., Trans-cellular propagation of Tau aggregation by fibrillar species. J Biol Chem 287, 19440-19451 (2012).
Khan et al., Tau: The Center of a Signaling Nexus in Alzheimer's Disease. Front Neurosci 10, 31 (2016).
Kimura et al., Alternative splicing of ryr1 alters the efficacy of skeletal ec coupling, CellCalcium, 2009;45:264-274.
Kjaergaard et al., Oligomer Diversity during the Aggregation of the Repeat Region of Tau. ACS Chem Neurosci 9, 3060-3071 (2018).
Klegeris et al., Toxicity of human monocytic THP-1 cells and microglia toward SH-SY5Y neuroblastoma cells is reduced by inhibitors of 5-lipoxygenase and its activating protein FLAP. J Leukoc Biol 73, 369-378 (2003).
Kleinfelder, Proc SPIE, 2003;4858:316.
Knutson et al., Chem Phys Lett, 1983; 102:501.
Ko et al., Cellular Models for Tau Filament Assembly. J Mole Neurosci 19, 311-316 (2003).
Kobayashi et al., Dantrolene Stabilzes Domain Interactions within the Ryanodine Receptor, JBiolChem, Feb. 25, 2005; 280(8):6580-6587.
Kobayashi et al., Dantrolene, a therapeutic agent for malignant hyperthermia, markedly improves the function of failing cardiomyocytes by stabilizing interdomain interactions within the ryanodine receptor, JAmCollCardiol, 2009;53:1993-2005.
Kobayashi et al., CircJ., 2010;74:2579-2584.
Kolarova et al., Structure and pathology of tau protein in Alzheimer disease. Int J Alzheimers Dis 2012, 731526 (2012) doi: 10.1155/2012/731526.
Kopeikina et al., Soluble forms of tau are toxic in Alzheimer's disease. Transl Neurosci 3, 223-233 (2012).
Kovacs, Invited review: Neuropathology of tauopathies: principles and practice. Neuropathol Appl Neurobiol 41, 3-23 (2015).
Krause et al., Anaesthesia, 2004;59:364-373.
Kuret et al., Evaluating triggers and enhancers of tau fibrillization. Microsc Res Tech 67, 141-155 (2005).
Lagalwar et al., Methods Mol Biol, 2013;1010:201-209.
Lakowicz et al. Principles of Fluorescence Spectroscopy, 3rd ed. Springer, New York, 2006; Table of Contents and Index.
Lanner, Ryanodine Receptors: Structure, Expression, Molecular Details, and Function in Calcium Release 2010 Cold Spring Harb Perspectives in Biology, 2:1-21.
Lasagna-Reeves et al., Identification of oligomers at early stages of tau aggregation in Alzheimer's disease. FASEB J 26, 1946-1959 (2012).
Lebakken et al., A Fluorescence Lifetime-Based Binding Assay to Characterize Kinase Inhibitors, J Biomol Screening, 2007; 12:828.
Lee et al., Three Dimensional Human Neuro-Spheroid Model of Alzheimer's Disease Based on Differentiated Induced Pluripotent Stem Cells. PLoS One 11, e0163072 (2016).
Li et al., A phosphorylation of the ryanodine does not affect calcium sparks in mouse ventricular myocytes, CircRes, 2002;90:309-316.
Li et al., Deletions of the Aequorea victoria green fluorescent protein define the minimal domain required for fluorescence. J Biol Chem 272, 28545-28549 (1997).
Li et al., Electrophoresis, 2014;35(12-13):1846.
Liu et al., Dynamic, inter-subunit interactions between the N-terminal and central mutation regions of cardiac ryanodine receptors, J Cell Sci, 2010;123:1775-1784.
Lo Cascio et al., Azure C Targets and Modulates Toxic Tau Oligomers. ACS Chem Neurosci 9, 1317-1326 (2018).
Lo et al., Discovery of Novel Small-Molecule Inhibitor of Tau Oligomerization by FRET-Based High-Throughput Screening, Poster, 1 page, Sep. 24, 2018.
Lo et al., Manipulation of Tau Oligomerization and Aggregation Characterized by Time-Resolved FRET, 2906-Pos Board B114, Feb. 2, 2018, pp. 585a-586a.
Lo et al., Manipulation of Tau Oligomerization and Aggregation Characterized by Time-Resolved FRET, *2906-Pos Board B114*, Poster, 1 page, Feb. 21, 2018.
Lutz et al., Novel approach for accurate tissue-based protein colocalization and proximity microscopy. Sci Rep 7, 2668 (2017).
MacDonald et al., Assembly of transgenic human P301S Tau is necessary for neurodegeneration in murine spinal cord. Acta Neuropathol Commun 7, 44 (2019).
MacLennan et al., Phospholamban: a crucial regulator of cardiac contractility, Nature Reviews, 2003;4:666-678.
Maeda et al., Increased levels of granular tau oligomers: an early sign of brain aging and Alzheimer's disease. Neurosci Res 54, 197-201 (2006).
Majid et al., In vivo axonal transport deficits in a mouse model of fronto-temporal dementia. Neuroimage Clin 4, 711-717 (2014).
Maltman et al., Chem Commun, 2010;46:6929.
Mancini et al., 5-Lipoxygenase-activating protein is the target of a novel hybrid of two classes of leukotriene biosynthesis inhibitors. Mol Pharmacol 41, 267-272 (1992).
Marks, Calcium cycling proteins and heart failure: Mechanisms and therapeutics, J Clin Invest, 2013;123:46-52.
Marquez et al., Curr Drug Targets, 2011; 12:600-620.
Maruyama et al., Mutation of aspartic acid-351, lysine-352, and lysine-515 alters the Ca2+ transport activity of the Ca2+-ATPase expressed in COS-1 cells, PNAS USA, 1988;85:3314-3318.
Marx et al., CircRes, 2001;88:1151-1158.
Maxwell et al., AmJPhysiolHeartCircPhysiol., 2012;302:H953-63.
McMurray et al., EurHeartJ, 1993;14:1493-1498.
Medina, An Overview on the Clinical Development of Tau-Based Therapeutics. Int J Mol Sci 19, (2018).
Meng et al., Orientation-based FRET sensor for real-time imaging of cellular forces, J Cell Sci, 2012;125:743.
Michelangeli et al., A diversity of SERCA Ca2+ pump inhibitors, Biochem Soc Trans, 2011;39:789-797.
Mirbaha et al., Inert and seed-competent tau monomers suggest structural origins of aggregation. Elife 7, (2018).
Moger et al., Screening, 2006;11:765.
Mondragon-Rodriguez et al., Phosphorylation of tau protein as the link between oxidative stress, mitochondrial dysfunction, and connectivity failure: implications for Alzheimer's disease. Oxid Med Cell Longev 2013, 940603 (2013).
Morine et al., Overexpression of SERCA1a in the mdx diaphragm reduces susceptibility to contraction-induced damage, Hum Gene Ther, 2010; 21:1735-1739.
Moussaud et al., Alpha-synuclein and tau: teammates in neurodegeneration? Mol Neurodegener 9, 43 (2014).
Mueller et al., Direct detection of phospholamban and sarcoplasmic reticulum Ca-ATPase interaction in membranes using fluorescence resonance energy transfer, Biochemistry, 2004;43:8754-8765.
Mueller et al., SERCA structural dynamics induced by ATP and calcium, Biochemistry, 2004;43:12846-12854.
Muraya et al., Benzbromarone Attenuates Oxidative Stress in Angiotensin II- and Salt-Induced Hypertensive Model Rats. Oxid Med Cell Longev 2018, 7635274 (2018).
Muretta et al., Direct real-time detection of the actin-activated power stroke within the myosin catalytic domain, Proc Acad Natl Sci USA, 2013;110:7211-7216.
Nath et al., The conformational ensembles of alpha-synuclein and tau: combining single-molecule FRET and simulations. Biophys J 103, 1940-1949 (2012).
Nesmelov et al., Proc Acad Natl Sci USA, 2011;108(5):1891.
Nouar et al., FRET and FRAP imaging: approaches to characterise tau and stathmin interactions with microtubules in cells. Biol Cell 105, 149-161 (2013).
Oda et al., Defective Regulation of interdomain interactions within ryanodine receptor plays a key role in the pathogenesis of heart failure, Circulation, 2005;111:3400-3410.

(56) References Cited

OTHER PUBLICATIONS

Oda et al., In Cardiomyocytes, Binding of Unzipping Peptide Activates Ryanodine Receptor 2 and Reciprocally Inhibits Calmodulin binding, Circulation, 2013;112:487-497.
Ono et al., CardiovasRes, 2010;87:609-617.
Orr et al., A Brief Overview of Tauopathy: Causes, Consequences, and Therapeutic Strategies. Trends Pharmacol Sci 38, 637-648 (2017).
Ozsoy et al., Oxidative stress promotes ligand-independent and enhanced ligand-dependent tumor necrosis factor receptor signaling. J Biol Chem 283, 23419-23428 (2008).
Park et al., Sarco(endo)plasmic reticulum Ca2+-ATPase 2b is a major regulator of endoplasmic reticulum stress and glucose homeostasis in obesity, Proc Natl Acad Sci USA, 2010;107:19320-19325.
Paterson et al., A fluorescence lifetime-based assay for serine and threonine kinases that is suitable for high-throughput screening, Anal Biochem, 2010;402:54.
Paul-Pletzer et al., Biochem J, 2005;387:905-909.
Petegem, Ryanodine Receptors: Structure and Function Sep. 2012 The Journal of Biological Chemistry, 287(38):31624-3632.
Picht et al., Sparkmaster: Automated calcium Spark Analysis with ImageJ, Am J Physiol Cell; Physiol, :2007;293:C1073-C1081.
Polanco et al., Extracellular Vesicles Isolated from the Brains of rTg4510 Mice Seed Tau Protein Aggregation in a Threshold-dependent Manner. J Biol Chem 291, 12445-12466 (2016).
Prestle et al., Overexpression of FK506-binding protein FKBP12.6 in cardiomyocytes reduces ryanodine receptor-mediated Ca(2+) leak from the sarcoplasmic reticulum and increases contractility, CircRes, 2001;88:188-194.
Priori et al., Inherited dysfunction of sarcoplasmic reticulum Ca2+ handling and arrhythmogenesis, CircRes, 2011;108:871-883.
Pritz et al., A Fluorescence Lifetime-Based Assay for Abelson Kinase, J Biomol Screening, 2011;16(1): 65-72.
Pritz et al., Fluorescence lifetime assays: current advances and applications in drug delivery, Expert Opinion on Drug Discovery, pp. 663-670, (2011).
Qin et al., JAmHeartAssoc, 2013;2:e000184.
Raina et al., PLoSOne, 2012;7:e38594.
Raja et al., Self-Organizing 3D Human Neural Tissue Derived from Induced Pluripotent Stem Cells Recapitulate Alzheimer's Disease Phenotypes. PLoS One 11, e0161969 (2016).
Rane et al., Curcumin Inhibits Tau Aggregation and Disintegrates Preformed Tau Filaments in vitro. J Alzheimers Dis 60, 999-1014 (2017).
Rhein et al., Amyloid-beta and tau synergistically impair the oxidative phosphorylation system in triple transgenic Alzheimer's disease mice. Proc Natl Acad Sci U S A 106, 20057-20062 (2009).
Robia et al., Forster Transfer Recovery Reveals That Phospholamban Exchanges Slowly From Pentamer but Rapidly From the SERCA Regulatory Complex, Circulation Research, pp. 1123-1129 (2007).
Rodriguez et al., Structure of the toxic core of alpha-synuclein from invisible crystals. Nature 525, 486-490 (2015).
Rolland et al., Sarcopenia: Its assessment, etiology, pathogenesis, consequences and future perspectives, J Nutr Health Aging, 2008;12:433-450.
Romo et al., Minimal Nucleation State of alpha-Synuclein Is Stabilized by Dynamic Threonine-Water Networks. ACS Chem Neurosci 8, 1859-1864 (2017).
Sahara et al., Assembly of tau in transgenic animals expressing P301L tau: alteration of phosphorylation and solubility. JNeurochem 83, 1498-1508 (2002).
Sahara et al., Tau oligomerization: a role for tau aggregation intermediates linked to neurodegeneration. Curr Alzheimer Res 5, 591-598 (2008).
Sambrook et al., Molecular Cloning: A Laboratory Manual, Cold Spring Harbor Laboratory Press, 1989.
Samso et al., Apocalmodulin and Ca2+-calmodulin bind to neighboring locations on the ryanodine receptor, JBiolChem, Jan. 11, 2002;277(2):1349-1353.
Samso et al., Structural Characterization of the RyR1-FKBP12 interaction, J Mol Biol, 2006;356:917-927.
Santacruz et al., Tau suppression in a neurodegenerative mouse model improves memory function. Science 309, 476-481 (2005).
Saunders et al. Characterization of a tau FRET biosensor sensitive to tau intramolecular folding. Program No. 048.14. 2018 Neuroscience Meeting Planner. San Diego, CA: Society for Neuroscience, 2018. Online. Nov. 3, 2018.
Schulz et al., A new link to mitochondrial impairment in tauopathies. Mol Neurobiol 46, 205-216 (2012).
Shan et al., JClinInvest, 2010;120:4375-4387.
Sharma et al., Tau monomer encodes strains. Elife 7, (2018).
Shin et al., Visualization of Tau(-)Tubulin Interaction in a Living Cell Using Bifluorescence Complementation Technique. Int J Mol Sci 19, 2978 (2018).
Simeonov et al., Fluorescence Spectroscopic Profiling of Compound Libraries, J Med Chem, 2008;51:2363.
Song et al., Differential integration of Ca2+-calmodulin signal in intact ventricular myocytes at low and high affinity Ca2+-calmodulin targets, JBiolChem, 2008;283:31531-31540.
Song et al., J Biol Chem, 2011;286:9120-9126.
Squire et al., Red-edge anisotropy microscopy enables dynamic imaging of homo-FRET between green fluorescent proteins in cells. J Struct Biol 147, 62-69 (2004).
Stange et al., JBiolChem., 2003;278:51693-51702.
Stergiopoulous et al., BMC Health Serv Res, 2012;12:345.
Sultana et al., Oxidative modification of brain proteins in Alzheimer's disease: perspective on future studies based on results of redox proteomics studies. J Alzheimers Dis 33 Suppl 1, S243-251 (2013).
Szollosi et al., CommunicationsinClinicalCytometry, 1998;34:159-179.
Tak et al., Bimolecular fluorescence complementation; lighting-up tau-tau interaction in living cells. PLoS One 8, e81682 (2013).
Taniguchi et al., Inhibition of heparin-induced tau filament formation by phenothiazines, polyphenols, and porphyrins. J Biol Chem 280, 7614-7623 (2005).
Tateishi et al., Defective domain-domain interactions within the ryanodine receptor as a critical cause of diastolic Ca2+ leak in failing hearts, CardiovascRes, 2009;81:536-545.
Tazzeo et al. the NADPH oxidase inhibitor diphenyleneiodonium is also a potent inhibitor of cholinesterases and the internal Ca(2+) pump, Br J Pharmacol, 2009;158:790-796.
Terentyev et al., CircRes, 2008;103:1466-1472.
Theillet et al., Structural disorder of monomeric alpha-synuclein persists in mammalian cells. Nature 530, 45-50 (2016).
Thomas et al., PNAS USA, 1978;75:5746-5750.
Thorne et al., Apparent activity in high-throughput screening: origins of compound-dependent assay interference, Curr Opin Chem Biol, 2010; 14:315.
Timm et al., Microtubule affinity regulating kinase activity in living neurons was examined by a genetically encoded fluorescence resonance energy transfer/fluorescence lifetime imaging-based biosensor: inhibitors with therapeutic potential. J Biol Chem 286, 41711-41722 (2011).
Tramier et al., Fluorescence anisotropy imaging microscopy for homo-FRET in living cells. Methods Cell Biol 85, 395-414 (2008).
Tramier et al., Sensitivity of CFP/YFP and GFP/mCherry pairs to donor photobleaching on FRET determination by fluorescence lifetime imaging microscopy in living cells. Microsc Res Tech 69, 933-939 (2006).
Tung et al., The amino-terminal disease hotspot of ryanodine receptors forms a cytoplasmic vestibule, Nature, 2010;468:585-588.
Tuttle et al., Solid-state NMR structure of a pathogenic fibril of full-length human alpha-synuclein. Nat Struct Mol Biol 23, 409-415 (2016).
Uchinoumi et al., Catecholaminergic polymorphic ventricular tachycardia is caused by mutation-linked defective conformational regulation of the ryanodine receptor, CircRes, 2010;106:1413-1424.
Valentin et al., Photoconversion of YFP into a CFP-like species during acceptor photobleaching FRET experiments. Nat Methods 2, 801 (2005).
Valera et al., Modulation of 5-lipoxygenase in proteotoxicity and Alzheimer's disease. J Neurosci 33, 10512-10525 (2013).

(56) References Cited

OTHER PUBLICATIONS

Valley et al., Tumor Necrosis Factor-related Apoptosis-inducing Ligand (TRAIL) Induces Death Receptor 5 Networks That Are Highly Organized, J Biol Chem, 2012;287:21265-21278.
Verheyen et al., Using Human iPSC-Derived Neurons to Model TAU Aggregation. PLoS One 10, e0146127 (2015).
Vunnam et al., Soluble Extracellular Domain of Death Receptor 5 Inhibits TRAIL-Induced Apoptosis by Disrupting Receptor-Receptor Interactions. J Mol Biol 429, 2943-2953 (2017).
Wagner et al., CircRes, 2011;108:555-565.
Wang et al., Localization of an NH(2)-terminal disease-causing mutation hot spot to the clamp region in the three-dimensional structure of the cardiac ryanodine receptor, JBiolChem, 2007;282:17785-17793.
Wang et al., Binding and neurotoxicity mitigation of toxic tau oligomers by synthetic heparin like oligosaccharides. Chem Commun (Camb) 54, 10120-10123 (2018).
Wang et al., JBiolChem, 2011;286:12202-12212.
Wang et al., Tau in physiology and pathology. Nat Rev Neurosci 17, 22-35 (2016).
Wang et al., Triclosan Enhances the Clearing of Pathogenic Intracellular *Salmonella* or Candida albicans but Disturbs the Intestinal Microbiota through mTOR-Independent Autophagy. Front Cell Infect Microbiol 8, 49 (2018).
Ward et al., Tau oligomers and tau toxicity in neurodegenerative disease. Biochem Soc Trans 40, 667-671 (2012).
Weaver et al., Conformational change as one of the earliest alterations of tau in Alzheimer's disease. Neurobiol Aging 21, 719-727 (2000).
Wehrens et al., FKBP12.6 deficiency and defective calcium release channel (ryanodine receptor) function linked to exercise-induced sudden cardiac death, Cell, 2003;113:829-840.
Wehrens et al., Ryanodine receptor/calcium release channel PKA phosphorylation: A critical mediator of heart failure progression, PNAS USA, 2006;103:511-518.
Weissmann et al., Microtubule binding and trapping at the tip of neurites regulate tau motion in living neurons. Traffic 10, 1655-1668 (2009).
Wischik et al., Selective inhibition of Alzheimer disease-like tau aggregation by phenothiazines. Proc Natl Acad Sci U S A 93, 11213-11218 (1996).
Wittmann et al., Tauopathy in *Drosophila*: neurodegeneration without neurofibrillary tangles. Science 293, 711-714 (2001).
Wobst et al., The green tea polyphenol (−)-epigallocatechin gallate prevents the aggregation of tau protein into toxic oligomers at substoichiometric ratios. FEBS Lett 589, 77-83 (2015).
Wood et al., Neurofibrillary tangles of Alzheimer disease share antigenic determinants with the axonal microtubule-associated protein tau (tau). Proc Natl Acad Sci U S A 83, 4040-4043 (1986).
Xia et al., Impaired tau-microtubule interactions are prevalent among pathogenic tau variants arising from missense mutations. J Biol Chem 294, 18488-18503 (2019).
Xiao et al., Removal of FKBP12.6 does not alter the conductance and activation of the cardiac ryanodine receptor or the susceptibility to stress-induced ventricular arrhythmias, J Biol Chem, 2007;282:34828-34838.
Xu et al., Defective calmodulin binding to the cardiac ryanodine plays a role in CPVT-associated channel dysfunction, BiochemBiophysResComm, 2010;394:660-666.
Yamaguchi et al., Molecular basis of calmodulin binding to cardiac muscle Ca(2+) release channel (ryanodine receptor), J Biol Chem, 2003;278:23480-23486.
Yamaguchi et al., JClinInvest, 2007;117:1344-1353.
Yamamoto et al., Peptide Probe study of the critical regulatory domain of the cardiac ryanodine receptor, BiochemBiophysResCommun, 2002;291:1102-1108.
Yamamoto et al., Postulated role of interdomain interaction within the ryanodine receptor Ca(2+) channel regulation, JBiolChem, 2000;275:11618-11625.
Yamamoto et al., Spectroscopic Monitoring of Local Conformational Changes during the Intramolecular Domain-Domain Interaction of the Ryanodine Receptor, Biochem, 2002;41(5):1492-1501.
Yan et al., Bidirectional regulation of Ca21 sparks by mitochondria-derived reactive oxygen species in cardiac myocytes, CardiovasRes, 2008;77:432-441.
Yang et al., In situ measurement of RyR2-calmodulin binding in permeablized cardiomyocytes, Biophys J, 2011;100:413a-414a.
Yang et al., CircRes, 2014;114:295-306.
Yano et al., Altered stoichiometry of FKBP12.6 versus ryanodine receptor as a cause of abnormal Ca(2+) leak through ryanodine receptor in heart failure, Circulation, 2000;2131-2136.
Yano et al., Circulation, 2005;112:3633-3643.
Yasar et al., Antihypertensive drugs decrease risk of Alzheimer disease: Ginkgo Evaluation of Memory Study. Neurology 81, 896-903 (2013).
Yoshiyama et al., Synapse loss and microglial activation precede tangles in a P301S tauopathy mouse model. Neuron 53, 337-351 (2007).
Yuan et al., Genetic mapping of targets mediating differential chemical phenotypes in Plasmodium falciparum, Nat Chem Biol, 2009;5:765-771.
Zacharias et al., Partitioning of lipid-modified monomeric GFPs into membrane microdomains of live cells. Science 296, 913-916 (2002).
Zhang et al., A Simple Statistical Parameter for Use in Evaluation and Validation of High Throughput Screening Assays. J Biomol Screen 4, 67-73 (1999).
Zhang et al., In-Cell NMR Study of Tau and MARK2 Phosphorylated Tau. Int J Mol Sci 20, (2018).
Zhao et al., A role of P301L tau mutant in anti-apoptotic gene expression, cell cycle and apoptosis. Mol Cell Neurosci 24, 367-379 (2003).
Zhao et al., Caspase-2 cleavage of tau reversibly impairs memory. Nat Med 22, 1268-1276 (2016).
Zigoneanu et al., Interaction of alpha-synuclein and a cell penetrating fusion peptide with higher eukaryotic cell membranes assessed by (1)(9)F NMR. Mol Pharm 9, 1024-1029 (2012).
Zima et al., J Physiol., 2010;588:4743-4757.

* cited by examiner a b c

METHODS TO IDENTIFY MODULATORS OF ACTIN-BINDING PROTEINS

CROSS-REFERENCE TO RELATED APPLICATIONS

This application claims the benefit of U.S. Provisional Application Ser. No. 62/859,864, filed Jun. 11, 2019, which is incorporated by reference herein in its entirety.

GOVERNMENT FUNDING

This invention was made with government support under AG026160, and GM032961 awarded by the National Institutes of Health. The government has certain rights in the invention.

SUMMARY OF THE APPLICATION

Some human diseases are linked to mutations within the actin-binding domains of actin-binding proteins. Frequently, the mutations result in increased binding of the actin-binding protein to actin. There are no cures or treatments for these diseases. The inventors have determined how to monitor, in real time, in live cells, the intermolecular interactions between three proteins and identify compounds that alter the intermolecular interactions. Two of the proteins are different actin-binding proteins, and the third protein is an actin filament. The intermolecular interactions that can be monitored include the interactions of the two actin-binding proteins with the actin filament to form a ternary complex.

Definitions

As used herein, the term "protein" refers broadly to a polymer of two or more amino acids joined together by peptide bonds. The term "protein" also includes molecules that contain more than one protein joined by disulfide bonds, ionic bonds, or hydrophobic interactions, or complexes of polypeptides that are joined together, covalently or noncovalently, as multimers (e.g., dimers, trimers, tetramers). Thus, the terms peptide, oligopeptide, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the terms "FRET," "fluorescence resonance energy transfer," "Förster resonance energy transfer" and "resonance energy transfer" are used interchangeably, and refer to a nonradiative energy transfer process that occurs between two chromophores.

As used herein, a "chromophore" is a molecule that includes a region that adsorbs certain wavelengths of light and interacts with such a region of another chromophore so as to be useful for FRET. Chromophores suitable for use in a FRET assay are known to the skilled person and are readily available. In one embodiment, a chromophore may be a donor (also referred to as a donor probe). A donor probe refers to a molecule that will absorb energy and then re-emit at least a portion of the energy over time. In one embodiment, a chromophore may be an acceptor (also referred to as an acceptor probe). An acceptor probe refers to a molecule that will accept energy nonradiatively from a donor, thus decreasing the donor's emission intensity and excited-state lifetime. Thus, provided that a donor probe and an acceptor probe are physically located sufficiently close (most often within 2.5 to 12 nm), the two probes function together and, upon excitation with an appropriate wavelength, the donor probe transfers a precise amount of energy (proportional to the negative sixth power of the donor-acceptor distance) to the acceptor probe. This process can be specifically and quantitatively detected by observing the decrease in donor fluorescence intensity or lifetime or, in some cases, also the energy re-emitted by the acceptor probe as fluorescence. Thus, FRET assays are typically used to measure (1) the mole fraction of donors coupled with acceptor (e.g., to determine the binding affinity between the donor-labeled and acceptor-labeled molecules) and (2) the distance and/or distance changes between donor and acceptor. When donor and acceptor are both attached to the same molecule, FRET can be used to detect a change in the molecule's structure. When donor and acceptor are attached to different molecules, FRET can be used to detect a change in the relative positions (e.g., binding, orientation) and structures of the two molecules. In one embodiment, when a fluorescent dye is attached to a protein, changes in fluorescence of the dye can be used to detect a change in the structure of the protein.

As used herein, the term "high-throughput screening" or "HTS" refers to a method drawing on different technologies and disciplines, for example, optics, chemistry, biology or image analysis, to permit rapid analysis of multiple samples at rates that permit highly parallel biological research and drug discovery. Typically, HTS includes a step of detecting FRET in a sample, with the detection taking no longer than 10, no longer than 6, or no longer than 3 minutes to read all wells of a 384-well or a 1536-well plate.

As used herein, the term "wild-type" refers to the most typical form of an organism, protein, or characteristic as it occurs in nature.

As used herein, "genetically engineered cell" and "genetically modified cell" are used interchangeably and refer to a cell into which has been introduced one or more exogenous polynucleotides and has been altered "by the hand of man." A cell is a genetically engineered cell by virtue of introducing one or more exogenous polynucleotides or transgenes, that encode the two proteins described herein (e.g., one transgene encodes a donor probe and another transgene encodes an acceptor probe) as heterologous proteins. In one embodiment, the genetically engineered cell includes more than one exogenous polynucleotide. In one embodiment, the exogenous polynucleotides are integrated into the cell genome and the encoded proteins are stably expressed. The exogenous polynucleotide is not diluted through mitosis and/or degraded (expression of the protein is not transient). In another embodiment, the engineered cell is one that transiently expresses one or more exogenous polynucleotides.

As used herein, an "exogenous polynucleotide" refers to a polynucleotide that is not normally or naturally found in a cell, or a polynucleotide that is present in a cell by human intervention.

As used herein, a "heterologous protein" refers to a protein that is not normally or naturally found in a cell, or a protein that is present in a cell by human intervention As used herein, "coefficient of variation" (CV) refers to a normalized measure of dispersion of a probability distribution or frequency distribution and is defined as the ratio of the standard deviation to the mean.

As used herein, "substantially free of" a material refers to a cell or a composition having less than 10% of the material, less than 5% of the material, less than 4% of the material, less than 3% of the material, less than 2% of the material, or less than 1% of the material. In one embodiment, the presence of the material in a composition is undetectable.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Conditions that are "suitable" for an event to occur, such as expression of a protein described herein or binding of a protein to an actin filament, or "suitable" conditions are conditions that do not prevent such events from occurring. Thus, these conditions permit, enhance, facilitate, and/or are conducive to the event.

As used herein, "providing" in the context of a genetically engineered cell, a composition, an article, or a test compound means making the genetically engineered cell, composition, article, or test compound, purchasing the genetically engineered cell, composition, article, or test compound, or otherwise obtaining the genetically engineered cell, composition, article, or test compound.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

As appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

(FIG. 2a) Model of GFP-ABD-L253P and Lifeact-mCherry bound to F-actin. Position of ABD on actin was based on 6ANU (Avery et al., Nat Commun, 2017, 8, 1350, doi:10.1038/541467-017-01367-w). The Lifeact binding site is based on the myosin-actin-binding structure (Holmes et al., Nature 2003, 425, 423-427, doi:10.1038/nature02005), due to the sequence similarities between Lifeact and myosin in actin-binding site. (FIG. 3b) Overlap of actin-binding regions in Lifeact and chicken myosin found using a BLAST search.

(FIG. 2a) Total (GFP-ABD and Lifeact-mCherry) and non-specific (GFP-ABD and mCherry) FRET with shifting donor (GFP) to acceptor (mCherry) ratios in HEK293-6E cells. Total and non-specific FRET is abolished by addition of 0.1% Triton X100 for cell lysis. The non-specific FRET readout demonstrates an increase in non-specific contribution to the total FRET with an increase in Lifeact-mCherry expression (n=3) (FIG. 2b) Effect of swinholide A (3 µM) and other actin-binding compounds (50 µM) on total FRET (GFP-ABD L253P plus Lifeact-mCherry) and non-specific FRET (GFP-ABD plus mCherry) in HEK293-6E cells. Data is shown as relative to DMSO control as mean±SD, n=3. (FIG. 2c) Co-sedimentation of ABD and actin shown as a representative Coomassie blue stain gel, and accrued data showing the ablation of ABD-L253P to actin-binding by 3 µM swinholide A (Swin A) and no significant effect of 50 µM tegaserod (Tegas) (n=4). (FIG. 2d) Co-sedimentation of Lifeact-mCherry and actin assays show that 3 µM swinholide A, not 50 µM tegaserod, reduces Lifeact-mCherry binding with actin. Data shown as relative to DMSO control as mean±SD, n=3-4. (FIG. 2e) Trypan blue based cell viability assay shows that 50 µM tegaserod, not 3 µM swinholide A, abolishes HEK293-6E cell viability. Data is shown as relative to DMSO control as mean±SEM, n=3-5. *Significantly different from DMSO control, $p<0.05$.

(FIG. 3a) Specific FRET dose-response of swinholide A shows reproducible EC50 values across plates read on the same day and different days. For each plate, each concentration was loaded over 64 wells on a 1536 well plate, n=3 plates. (FIG. 3b) Plot of excellent Z'-factor values for 1 µM swinholide A loaded over 768 wells vs DMSO control loaded over 768 wells on a 1536 well plate. Data shown per plate n=3.

(FIG. 4a) FLT data was acquired at three time points following FRET assay loading into 1536 well plates that were pre-loaded with 1280 library compounds (10 µM final) or DMSO control. Representative FRET response to LOPAC compounds, including interfering compounds. (FIG. 4b) Representative FRET response with interfering compounds removed demonstrates that many Hit compounds have a time dependent effect, with the greatest effect at 120 and 180 min following plate loading. (FIG. 4c) Relative FRET effect of LOPAC Hits that were identified (with 4SD threshold) in at least 2 of the 4 screens. n=4, data shown as mean±SEM.

(FIG. 6a) Co-sedimentation of Lifeact-mCherry and actin assays show that 3 µM swinholide A, and only 10 µM HTS Hits NPPB, GW7647, palmitoyl-DL-carnitine and calmidazolium reduce Lifeact-mCherry binding with actin. Data shown as relative to DMSO control as mean±SEM, n=3-5. (FIG. 6b) Trypan blue based cell viability assay shows that 3 hr incubation with 10 µM GW7647, palmitoyl-DL-carnitine and calmidazolium, reduces HEK293-6E cell viability. Data shown as relative to DMSO control as mean±SEM, n=3-5. (FIG. 6c) Co-sedimentation of ABD and actin show that only 3 µM swiholide A, not 10 µM Hits, reduce ABD-L253P binding to actin. Data is shown as relative to DMSO control as mean±SEM, n=1. (FIG. 6d) Sedimentation of ABD L253P (without actin) assays is used to identify compounds that promote aggregation. Data show that 10 µM NPPB, GW7647, gossypol, olvanil, PPT, AMG 9810 and candesartan promote aggregation. Data is shown as relative to DMSO control as mean±SEM, n=1. * Significantly different from DMSO control, p<0.05.

(FIG. 10a) GFP-ABD-L253P was co-transfected with varying amounts of Lifeact-mCherry (mCh-Lifeact) or mCherry alone. mCherry intensities and FRET efficiencies were measured in HEK cells for each transfection condition. (FIG. 10b) Non-specific FRET between GFP-ABD-L253P and mCherry is modeled by non-linear regression. (FIG. 10c) FRET between GFP-ABD-L253P and Lifeact-mCherry is >/=80% specific when 40% or less of mCherry-Lifeact is transfected.

(FIG. 12a) FRET efficiencies measured for GFP-tagged wild-type and mutant ABDs of β-III-spectrin, dystrophin and α-actinin. (FIG. 12a) In vitro F-actin co-sedimentations assays, performed in triplicate, confirming FRET data that the L212P mutation in dystrophin increases actin-binding affinity.

Figure 1:
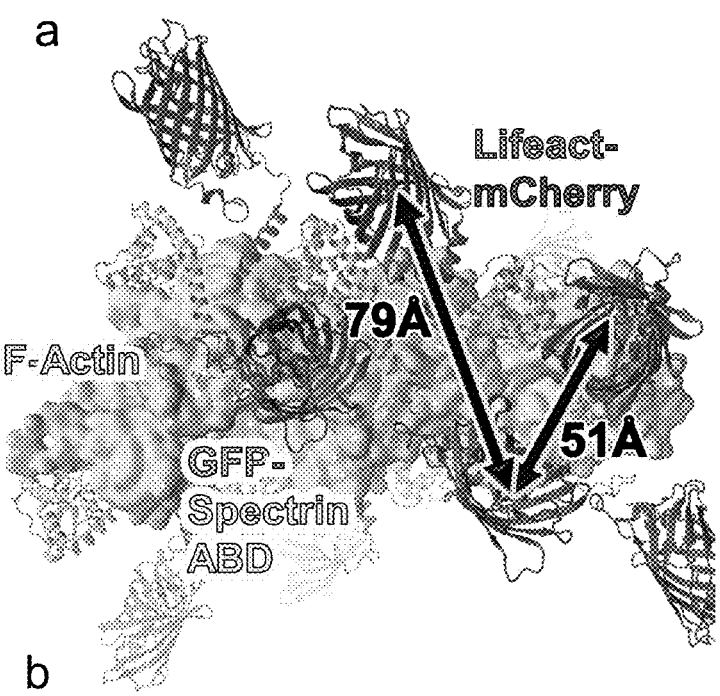
FIG. 1 shows a model of ABD biosensor.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION OF ILLUSTRATIVE EMBODIMENTS

Proteins

Provided herein are methods for identifying a compound that alters fluorescence resonance energy transfer (FRET) between two proteins bound to an actin filament. The alteration can be an increase or a decrease in FRET. In one embodiment, the alteration is a decrease in FRET. In one embodiment, a protein useful in the methods described herein binds an actin filament (also referred to as an actin polymer) and does not bind actin monomers at a detectable level.

The two proteins bound to an actin filament are actin-binding proteins and each includes an actin-binding domain (ABD). A protein is considered to be an actin-binding protein if it binds an actin filament under physiological conditions, and methods for evaluating whether a protein binds an actin filament under physiological conditions are known to the skilled person. In one embodiment, physiological conditions are conditions present within a cell.

In one embodiment, the ABD includes two tandem subdomains, termed calponin homology domains (CH). The two tandem CH subdomains are CH1 and CH2, and are typically closely associated with one another in a compact structural state. The two tandem CH subdomains are typically located near the N-terminal end of an actin-binding protein. An individual CH domain includes ~106 amino acids, and contains four major α-helices, several minor α-helices and connecting loops. These tandem-CH, actin-binding domains show high sequence conservation (Banuealos, 1998; PMID: 9817844). Examples of proteins containing a tandem-CH, actin-binding domain (referred to herein as a member of the tandem-CH, actin-binding domain family of proteins, and sometimes referred to in the art as the spectrin superfamily of proteins) include human β-I-spectrin, β-II-spectrin, β-III-spectrin, β-IV-spectrin, β-V-spectrin, α-actinin-1, α-actinin-2, α-actinin-3, α-actinin-4, dystrophin, utrophin, filamin-A, filamin-B, filamin-C, fimbrin, plectin, nesprin, microtubule and actin crosslinking protein (MACF1), and distonin. The amino acid sequences of these proteins are known and readily available to the skilled person.

In one embodiment, the ABD includes a CH1 from an actin-binding protein and the amino acids located between the CH1 and the N-terminal end of the protein, e.g., the ABD is a portion of the N-terminal end of a protein having a tandem-CH actin-binding domain. This type of fragment is referred to herein as a "CH domain-containing ABD." Examples of this type of protein are known (Avery, 2017: PMID: 29116080; Singh, 2017: PMID: 28443334; Iwamoto, 2018: PMID: 30224736; Harris, 2019: PMID: 31693446)).

Further, the skilled person can be easily identify the "CH domain-containing ABD" present in a protein having a tandem-CH actin-binding domain.

In another embodiment, the ABD includes a peptide sequence, such as the N-terminal amino acids of the yeast protein ABP140 (Riedl, 2008: PMID: 18536722; Wedlich-Soldner et al., U.S. Pat. No. 8,957,029), termed Lifeact. When attached to the fluorescent protein such as mCherry, Lifeact specifically binds actin filaments, with negligible affinity for monomeric actin (Courtemanche, 2016; PMID: 27159499).

An actin-binding protein used in a method described herein can have one or more mutations. A mutation can be one of those known in the art as associated with an increase or decrease in the ability of an actin-binding protein to bind an actin filament. In one embodiment, a mutation can be one that is known in the art as associated with disease in a human. For instance, at least one mutation is recognized as correlating to spinocerebellar ataxia type 5 (the L253P mutation of (3-III-spectrin (Ikeda, 2006; PMID: 16429157)). Other mutations that correlate with disease in β-III-spectrin include T62I, F160C, Y272H (Nicita, 2019; PMID: 31066025), H278R (Liu, 2016; PMID: 27748352), R437G (Mizuno, 2019; PMID: 30898343), R437W, R437Q (Nicita, 2019; PMID: 31066025), R480W (Jacob, 2013; PMID: 22914369), T472M (Cho, 2012; PMID: 22843192), E532_M544del (Ikeda, 2006; PMID: 164291547), L629_R634delinsW (Ikeda, 2006; PMID: 164291547), E870del (Wang, 2014; PMID: 25142508), and W2065*, where the asterisk "*" refers to a stop codon introduced in place of residue W2065 (Nicita, 2019; PMID: 31066025). Mutations in other actin-binding proteins that correlate with disease include R46Q, V105I and E225K (Clark, 2009; PMID: 19773341) in α-actinin-1; M228T (Girolami, 2014; PMID: 25173926) in α-actinin-2; L228E, T232L, S235P (Kaplan, 2000; PMID: 10700177), W59R, I149del (Weins, 2005; PMID: 16251236), and K255E (Weins, 2007; PMID: 17901210) in α-actinin-4; E254K (Clark, 2009; PMID: 19773341) in filamin A; W148R and M202V (Sawyer, 2009; PMID: 19505475) in filamin B; A193T and M251T (Duff, 2011; PMID: 21620354) in filamin C; and K18N, L54R, D165V, A168D, L172H and Y231N (Henderson, 2010; PMID: 20457930) in dystrophin.

In one embodiment, a mutation is one that increases the binding of an actin-binding protein to actin. In one embodiment, the increase of binding to actin of a mutant actin-binding protein compared to the wild-type protein can be at least 10-fold, at least 50-fold, at least 100-fold, at least 500-fold, or at least 1000-fold. In one embodiment, the increase of binding to actin of a mutant actin-binding protein compared to the wild-type protein can be no greater than 10,000-fold, no greater than 1000-fold, or no greater than 500-fold. Examples of such mutations are known and include, but are not limited to, L253P and K267E in β-III-spectrin. Mutations in other actin-binding proteins that increase actin-binding affinity include R46Q, V105I and E225K (Clark, 2009; PMID: 19773341) in α-actinin-1; M228T (Girolami, 2014; PMID: 25173926) in α-actinin-2; L228E, T232L, S235P (Kaplan, 2000; PMID: 10700177), W59R, I149del (Weins, 2005; PMID: 16251236), and K255E (Weins, 2007; PMID: 17901210) in α-actinin-4; E254K (Clark, 2009; PMID: 19773341) and Q170P (Iwamoto, 2018; PMID: 30224736) in filamin A; W148R and M202V (Sawyer, 2009; PMID: 19505475) in filamin B; A193T and M251T (Duff, 2011; PMID: 21620354) in filamin C; K278E in plectin (Harris, 2019; PMID: 31693446); Q33A and T36A in utrophin (Harris 2019; PMID: 31693446) and L212P in dystrophin. Without intending to be limiting, in some embodiments one class of mutations cause the CH1 and CH2 domains to be in an "open" state and have higher binding to actin.

Each actin-binding protein used in the methods described herein includes a heterologous domain. As used herein, a "heterologous domain" refers to a foreign sequence, e.g., an amino acid sequence (such as a fluorescent protein or a domain to which a fluorescent dye can attach such as an amino acid sequence or an unnatural amino acid) that is not normally part of a wild-type or naturally occurring protein. The heterologous domain may be a donor probe or an acceptor probe. The heterologous domain may be a fluorescent protein or may be a domain to which a fluorescent dye can attach.

A heterologous domain may be present at any location in an actin-binding protein. For instance, a heterologous domain can be present at the amino-terminal end, the carboxy-terminal end, or any location between. Thus, a heterologous domain can be at any location within an actin-binding protein. However, while the two heterologous domains can be independently located, the two heterologous domains are present at two locations that are in a spatial proximity that is close enough to allow FRET to occur between the two. Thus, in one embodiment, a first actin-binding protein (e.g., β-III-spectrin) includes a donor probe and a second actin-binding protein (e.g., Lifeact) includes an acceptor probe, where the distance between the two probes in the ternary structure of the two actin-binding proteins when bound to an actin filament is estimated to be no greater than 2 nanometers (nm), no greater than 4 nm, no greater than 6 nm, no greater than 8 nm, no greater than 10 nm, or no greater than 12 nm.

In one embodiment, the protein that is a member of the tandem-CH, actin-binding domain family of proteins includes the donor probe and the second protein, e.g., a Lifeact protein, includes the acceptor probe. In another embodiment, the protein that is a member of the tandem-CH, actin-binding domain family of proteins includes the acceptor probe and the second protein, e.g., a Lifeact protein, includes the donor probe.

The addition of a heterologous domain to an actin-binding protein may alter the function of the actin-binding protein in some way. Thus, in one embodiment, the function of an actin-binding protein that includes one heterologous domain has no detectable change in activity or behavior compared to the wild-type actin-binding protein that does not include the heterologous domain. In another embodiment, the function of an actin-binding protein that includes a heterologous domain has a detectable change. Actin-binding proteins useful in the methods described herein may have altered function but preserve one or more essential characteristics, e.g., the ability to bind actin, that can be analyzed as disclosed herein. In some embodiments, an actin-binding protein is a wild-type protein (in other words, it is a wild-type protein modified to include a heterologous domain), and in others the actin-binding protein can include one or more mutations which alter the function of that actin-binding protein. In one embodiment, the one or more mutations alter the actin-binding activity of the actin-binding protein, where the alteration can be an increase or a decrease in binding compared to the wild-type protein.

Methods for engineering an actin-binding protein to include one or more heterologous domains are known in the art and are routine. Typical locations for an inserted heterologous domain include the amino-terminus, the carboxy-terminus, and an internal site. An actin-binding protein used in the methods described herein can be produced using recombinant techniques, chemical or enzymatic synthesis, or be naturally occurring. An actin-binding protein can be isolated or can be present in a cell.

Chromophores suitable for the methods described herein are known to the skilled person and are routinely used. Examples of suitable chromophores include, but are not limited to, fluorescent proteins, including green fluorescent protein, including mClover3, red fluorescent protein, yellow fluorescent protein, and blue fluorescent protein. Green fluorescent protein and red fluorescent protein may be used as a donor-acceptor pair, and blue fluorescent protein and yellow fluorescent protein may be used as a donor-acceptor pair. The amino acid sequences of different version of green fluorescent protein, red fluorescent protein, yellow fluorescent protein, and blue fluorescent protein are known to the skilled person and are readily available, as are analogues of these proteins. Examples of red fluorescent proteins include, but are not limited to, mCherry and mRuby3. Other chromophores include fluorescent dyes that can be attached to a protein when the protein is present in a cell. Examples of such dyes are known in the art and are routinely used. Examples include dyes that react with cysteine, having reactive iodoacetamide, maleimide, or thiosulfonate groups. Other examples include the protein labeling reagent FLASH-EDT2, a dye that can react with the domain CCXXCC (SEQ ID NO:1) (Invitrogen), and SNAP-tag, a self-labeling protein tag (New England Biolabs). Other fluorescent dyes are available that react specifically with an unnatural amino acid that is incorporated into a protein by a modified tRNA. In one embodiment, a fluorescent dye is one that will pass through a cell membrane. Specific examples of fluorescent dyes include, but are not limited to, Alexa Fluor dyes.

Any appropriately selected two chromophores can be used as a donor-acceptor pair in the methods described herein, provided that the energy emitted by a donor (the emission spectrum) overlaps with the energy absorbed by an acceptor (the excitation spectrum), e.g., an energy transfer process (FRET) occurs between two chromophores. A donor and an acceptor that meet this overlap are referred to as a donor-acceptor pair. In one embodiment, donor-acceptor pairs are chosen such that interference from cell autofluorescence or test-compound fluorescence is minimized. Accordingly, in one embodiment, donors that can be excited at longer wavelengths are superior to those excitable at shorter wavelengths. For instance, donors that can be excited at wavelengths of greater than 300 nm, greater than 400 nm, or greater than 500 nm, are preferred in some embodiments. In some embodiment, red-shifted donors (greater than 600 nm, greater than 700 nm, or greater than 800 nm) can be used (Schaaf et al., 2018, Biosensors, 8(4):99). Also, probes with longer fluorescence lifetime (more than 3 nanoseconds (ns)) will be superior to probes with shorter fluorescence lifetime.

In one embodiment the donor-acceptor pair is selected so the Förster distance is at least 50 angstroms (Å), at least 52 Å, or at least 54 Å. Förster distance, also referred to as Förster constant, represents the molecular separation at which energy transfer between the donor and acceptor is 50% efficient. In one embodiment, useful donors include, but are not limited to, fluorescent proteins that can be excited at a wavelength of 473 nm and have an emission wavelength of 500-530 nm. Examples of such donors include, but are not limited to, green fluorescent protein and mClover3. In one embodiment, useful acceptors that can be used with such donors include, but are not limited to, fluorescent proteins having an excitation wavelength that is responsive to 550-590 nm and an emission wavelength of 590-610 nm. Examples of such acceptors include, but are not limited to, mCherry and mRuby3.

The actin-binding proteins are expressed in a cell that also expresses actin filaments. A polynucleotide sequence encoding an actin-binding protein with the heterologous domains can be readily produced by reference to the standard genetic code using known and routine methods, and the polynucleotide can be inserted into a vector. A vector is a replicating polynucleotide, such as a plasmid, phage, or cosmid, into which another polynucleotide may be inserted so as to bring about the replication of the inserted polynucleotide. Construction of vectors containing a polynucleotide encoding an actin-binding protein employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of the protein encoded by the coding region, i.e., an expression vector. The term vector includes, but is not limited to, plasmid vectors, viral vectors, cosmid vectors, or artificial chromosome vectors.

Methods

In the exemplary methods described herein, the experimental observations indicate that FRET detection of intermolecular interaction between two actin-binding proteins bound to an actin filament, one protein fused to a donor probe and one protein fused to an acceptor protein, provides measurable indications, in real time, of the binding of the actin-binding proteins to actin filaments in live cells. In one embodiment, methods of the present disclosure are directed to determining whether the ability of a protein to bind actin is altered in the presence of a test compound, where one actin-binding protein used in the method is believed to play a role in disease and includes one or more mutations that can alter actin binding, and the second actin-binding protein used in the method is used to aid in monitoring changes in binding of the first protein to actin.

The methods described herein use the lifetime of a chromophore instead of its intensity. A measuring instrument useful in the methods disclosed herein is a spectrometer that is compatible with FRET assays and can perform direct waveform recording to detect the entire time course of a time-resolved fluorescence decay with high quality (signal/noise>100) within 1 millisecond (ms) or less, in a microplate format that allows for the analysis of at least 100 samples per minute. An example of such an instrument is described by Petersen et al. (Rev Sci Instrum. 2014, 85(11):113101) and Schaaf et al. (SLAS Discov. 2017, 22(3): 250-261). An example of a laser suitable for the methods described herein is a passively Q-switched microchip laser (multi-wavelength series laser devices, model number FP2-473-3-10, manufactured by Concepts Research Corp., Charlotte, N.C., USA). An example of a digitizer suitable for the methods described herein is described in Pavicic (U.S. Pat. No. 6,816,102). An example of direct waveform recording suitable for the methods described herein is described in (Muretta, et al., 2010, *Rev Sci Instrum* 81:103101).

In one embodiment, FLT is measured using a format that permits rapid evaluation of multiple samples over a short period of time, e.g., a high throughput format. In one embodiment, such a format is a plate reader (FLT-PR).

FLT-PRs useful in the methods described herein are readily available (Fluorescence Innovations, Minneapolis, Minn.). The measurement of FLT by using direct waveform recording detection technology in a plate reader provides the precision to resolve small changes in FRET, and can scan the plate rapidly.

In one embodiment, a method includes identifying a compound that alters FRET between the two proteins. The method includes providing a genetically engineered cell that expresses the two proteins and exposing the cell to a test compound that is membrane permeant, thus forming a mixture with the two proteins inside the cell. One of the proteins has a first heterologous domain that includes a first probe, and the other protein has a second heterologous domain that includes a second probe. The first and second probes are a donor-acceptor pair. Both proteins are actin-binding proteins. Suitable actin-binding proteins are described herein. In one embodiment, one protein includes at least one mutation compared to a wild-type protein, and the at least one mutation optionally increases the binding affinity of the protein for actin compared to the same protein without the at least one mutation. The genetically engineered cell is one that expresses actin at a level suitable for the detection of FRET when the method is practiced.

The fluorescence lifetime of the donor probe, the acceptor probe, or a combination thereof is then measured. A difference between the fluorescence lifetime in the presence of the test compound and the fluorescence lifetime in the absence of the test compound indicates that the test compound alters the FRET between the donor and acceptor probes. An alteration in FRET may be due to the test compound directly interacting with one of the two heterologous proteins or the actin filament, altering cellular pathways that post-translationally modify one of the two heterologous proteins or the actin filament, or by acting through an indirect pathway. Methods for determining if a compound specifically and directly interacts with one of the two heterologous proteins or the actin filament are known and include, for instance, surface plasmon resonance (SPR) and transient phosphorescence anisotropy (TPA). Indirect pathways that non-specifically impact FRET and can lead to false positive results include test compounds that are intrinsically fluorescent, cytotoxic or cause aggregation of the actin-binding domain proteins. Methods for determining if a test compound acts through an indirect pathway include performing a counter screen. Briefly, a counter screen can include the same conditions used to initially evaluate a test compound, but one protein and its heterologous domain is replaced with just the heterologous domain. In one embodiment, a reduction of FRET can indicate a reduction in the actin-binding affinity of one or both actin-binding proteins. This reduction in binding affinity can identify test compounds that function to suppress aberrant binding sufficiently to reduce disease progression. A test compound identified using a method described herein is a potential therapeutic that can be modified by medicinal chemistry to develop related and/or more effective compounds that can be further tested in animal studies.

In one embodiment, the genetically modified cell is live. The genetically modified cell can be in suspension or adhered to a surface. Examples of cells useful in the methods described herein include eukaryotic cells and prokaryotic cells. Examples of eukaryotic cells include mammalian cells, such as vertebrate cells, e.g., human, murine (including mouse and rat), canine, or porcine cells. Examples of cells include, for instance, primary cells (e.g., cells that have recently been removed from a subject and are capable of limited growth in tissue culture medium), and cultured cells (e.g., cells that are capable of long-term culture in tissue culture medium). An example of a specific cell type is a neuronal cell. Other examples of eukaryotic cells include invertebrates (such as parasites, including helminths and protozoans such as *Plasmodium* spp.) and unicellular eukaryotic cells, such as yeast cells. Examples of prokaryotic cells include, for instance, *E. coli*. In some embodiments, a dysfunctional cell may be used. In one embodiment, a cell is one that can be cultured in suspension (e.g., non-adherent) and does not require contact with a surface for replication. In one embodiment, expression of the two heterologous proteins in a genetically modified cell is stable, e.g., one or more exogenous polynucleotides encoding the protein are integrated into the genomic DNA of a cell. In one embodiment, the expression of the two heterologous proteins in a genetically modified cell is transient. In one embodiment, the cells are lysed before FRET is measured. Methods for obtaining cell homogenates are known in the art.

A compound useful in the method includes, but is not limited to, an organic compound, an inorganic compound, a metal, a polypeptide, a non-ribosomal polypeptide, a polyketide, a peptidomimetic compound, or an aptamer. The sources for compounds that may alter activity of a protein described herein include, but are not limited to, chemical compound libraries, fermentation media of *Streptomycetes*, other bacteria and fungi, and cell extracts of plants and other vegetations. Small molecule libraries are available, and include AM:RI library, AnalytiCon, BioFocus DPI Library, Chem-X-Infinity, ChemBridge Library, ChemDiv Library, Enamine Library, The Greenpharma Natural Compound Library, Life Chemicals Library, LOPAC1280™, MicroSource Spectrum Collection, Pharmakon, The Prestwick Chemical Library®, SPECS, NIH Clinical Collection, Chiral Centers Diversity Library. In some embodiments, the number of compounds evaluated in an assay includes between 1 and 10,000,000 compounds, between 1 and 1,000,000 compounds, between 1 and 100,000 compounds, or between 1 and 1,000 test compounds.

Measuring the fluorescence lifetime of a donor probe, an acceptor probe, or both, of a cell that includes the two heterologous proteins and test compound mixture (e.g., a mixture present in a well) may occur over a specific time period. In one embodiment, the time period of measuring the fluorescence lifetime of a mixture is no greater than 5 seconds, no greater than 1 second, no greater than 0.5 seconds, no greater than 0.1 seconds, no greater than 0.01 seconds, no greater than 0.001 seconds, no greater than 0.0001 seconds, no greater than 0.00001 seconds, or no greater than 0.000005 seconds. This time period for measurement is distinct from the time period a donor probe fluoresces (i.e., the fluorescence lifetime of a donor probe), which is on the order of nanoseconds.

In one embodiment, the coefficient of variation (CV) obtained from a sample of cells that include the two heterologous proteins and test compound mixture (e.g., a mixture present in a well) is no greater than 1%, no greater than 0.5%, or no greater than 0.3%.

In one embodiment, a test compound can have a time dependent effect. Accordingly, a predetermined amount of time can elapse after mixing a test compound with the cells and reading any detectable FRET between the two probes. In one embodiment, at least 30, at least 60, at least 90, at least 120, or at least 180 minutes can elapse before FRET is measured.

In one embodiment, a waveform obtained from a sample of cells that include the two heterologous proteins and test compound mixture (e.g., a mixture present in a well) has a signal/noise (S/N) that is at least 100, at least 200, at least 300, or at least 400.

In certain embodiments, the FRET assays disclosed herein are measured at a single emission wavelength. In certain embodiments, the FRET fluorescence lifetime properties are measured at two or more wavelengths. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (for instance, round- or flat-bottom multi-well plates). Examples of multi-well plate formats that can be used in the methods provided herein include those found on 96-well plates (12×8 array of wells), 384-well plates (24×16 array of wells), 1536-well plate (48×32 array of well), 3456-well plates and 9600-well plates. Other formats that may be used in the methods provided herein include, but are not limited to, single or multi-well plates comprising a plurality of domains. In certain embodiments, the plates are opaque-wall, opaque -bottom plates. In certain embodiments, the plates are black-wall, black-bottom plates. In certain embodiments, the plates have black walls and clear bottoms in order to allow bottom excitation and reading of the fluorescence signals. In certain embodiments, the plates are chosen with minimal and uniform intrinsic fluorescence intensity within the range used in the method to avoid interference with the FRET signals.

Kits

Also provided herein are kits for identifying a compound that modulates the interaction between two actin-binding proteins and actin. A kit may include, in any combination, an actin-binding protein described herein labeled with a donor probe and a different actin-binding protein described herein labeled with an acceptor probe. The proteins can be present in a genetically modified cell, or the kit can include a polynucleotide, such as a vector, encoding one or more of the actin-binding proteins for use in transfecting a cell.

In certain embodiments, a kit may further include buffers and reagents useful for the procedure, and instructions for carrying out the assay. In certain embodiments, a kit may further include other useful agents, such as positive and negative control reagents, and the like. In one embodiment, swinholide A is included as a positive control.

Methods and kits disclosed herein may be carried out in numerous formats known in the art. In certain embodiments, the methods provided herein are carried out using solid-phase assay formats. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (for instance, round- or flat-bottom multi-well plates). Examples of multi-well plate formats that can be used in the methods provided herein include those found on 96-well plates (12×8 array of wells), 384-well plates (24×16 array of wells), 1536-well plate (48×32 array of well), 3456-well plates and 9600-well plates. Other formats that may be used in the methods provided herein include, but are not limited to, single or multi-well plates comprising a plurality of domains. In certain embodiments, the plates are opaque-wall, opaque -bottom plates. In certain embodiments, the plates are black-wall, black-bottom plates. In certain embodiments, the plates have black walls and clear bottoms in order to allow bottom excitation and reading of the fluorescence signals. In certain embodiments, the plates are chosen with minimal and uniform intrinsic fluorescence intensity within the range used in the method to avoid interference with the FRET signals.

EXAMPLES

The present invention is illustrated by the following examples. It is to be understood that the particular examples, materials, amounts, and procedures are to be interpreted broadly in accordance with the scope and spirit of the invention as set forth herein.

Example 1

Drug Discovery for Spinocerebellar Ataxia, Using Fluorescence Technology Targeting β-III-spectrin Abstract Numerous diseases are linked to mutations in the actin-binding domains (ABDs) of conserved cytoskeletal proteins, including β-III-spectrin, α-actinin, filamin, and dystrophin. A β-spectrin ABD mutation (L253P) linked to spinocerebellar ataxia type 5 (SCA5) causes a dramatic increase in actin-binding. Reducing actin-binding of this mutant is thus a potential therapeutic approach for SCA5 pathogenesis. Here, we validate a high-throughput screening (HTS) assay to discover disrupters of the actin and mutant β-III-spectrin ABD interaction in live cells. This assay monitors FRET between fluorescent proteins fused to the mutant ABD and the actin-binding peptide Lifeact, in HEK293-6E cells. We demonstrate HTS compatibility with an excellent Z'-factor of 0.67. We screened a library of 1280 pharmacologically active compounds and identified nine reproducible Hits that reduced FRET. Using these Hit compounds, we further validated a counter screen to eliminate false Hits resulting from cell lysis or ABD aggregation. The compound effect on actin-binding of ABD and/or Lifeact was confirmed using in vitro co-sedimentation assays. This report demonstrates high-throughput cell-based methods for primary and counter drug screening to identify small-molecule modulators of actin-binding for treatment of SCA5. Similar methodology may be used to identify therapeutics for a broad range of diseases linked to spectrin-related proteins.

1. Introduction

α-spectrin is one of several conserved cytoskeletal proteins, including α-actinin, filamin and dystrophin, with mutations in its N-terminal actin-binding domain (ABD) that are linked with human diseases [1-8]. β-III-spectrin forms a heterotetrameric complex with α-II-spectrin, and cross-links actin filaments to form a cytoskeleton localizing to the shafts and spines of Purkinje cell dendrites [9]. We recently determined the molecular consequence of an autosomal dominant mutation (L253P) in the ABD of β-III-spectrin that causes spinocerebellar ataxia type 5 (SCA5), a progressive neurodegenerative disease [10]. SCA5 is characterized neurologically by ataxia, dysarthria, and eye movement abnormalities such as gaze-evoked nystagmus [11]. A key pathological finding is cerebellar hypoplasia, the loss of Purkinje cells in the cerebellar cortex [11,12]. Intriguingly, our recent work revealed that a SCA5 associated missense mutation, L253P, causes a 1000-fold increase in actin-binding affinity [10]. Using *Drosophila*, we demonstrated that the SCA5 L253P mutation reduces the plasticity of the spectrin-actin cytoskeleton underlying the plasma membrane, leading to destabilization and loss of dendritic branches [13]. This suggests that the cellular mechanism underlying SCA5 pathogenesis is a Purkinje cell deficit connected to loss of dendritic arborization, resulting from elevated actin-binding affinity of the mutant α-III-spectrin. Thus, an effective therapeutic strategy for SCA5 should seek to ameliorate the aberrant actin affinity. Significantly, missense mutations in the highly conserved ABDs of α-actinin and filamin, have also been shown to cause increased actin-binding affinity [2-7]. Consequently, small molecules developed for SCA5 therapy may also be useful in treatment of diseases arising from ABD mutations in α-actinin and filamin.

The β-III-spectrin ABD is comprised of tandem calponin homology (CH) subdomains (CH1 and CH2) that are closely associated with one another in a compact structural state. Significantly, the leucine residue that is mutated in SCA5 is positioned at the interface between CH1 and CH2, providing hydrophobic contacts that stabilize the close apposition of the CH subdomains. Biophysical measurements indicated that when the L253P mutation is introduced, the ABD remains well-folded but becomes significantly destabilized [10]. This suggested that high-affinity actin-binding results from an "opening" of the ABD by disrupting the CH1/CH2 interface. We propose that small-molecule drugs targeting the mutant ABD, can reduce actin-binding by either: 1) promoting a shift from the "open" to "closed" conformation, or 2) masking residues in CH1 that are exposed in the "open" state and directly mediate interaction with actin. Moreover, because the mutant ABD populates the "open" conformation more significantly than wild-type, small molecules recognizing the "open" state should selectively target the mutant ABD over wild-type. The similar position of α-actinin and filamin disease mutations at the CH1/CH2 interface predicts the SCA5 structural mechanism of disease is conserved across the spectrin family of cytoskeletal proteins.

Currently there is no HTS assay that can measure the binding activity of mutant ABDs to actin filaments (F-actin), and can be implemented for drug discovery. Moreover, we are unaware of any effort to develop therapies for diseases resulting from dominant (gain-of-function) mutations in the spectrin family of cytoskeletal proteins. The binding of ABD proteins to actin filaments can be quantified in vitro by F-actin co-sedimentation assays using purified actin and ABD proteins [10]. However, these in vitro assays cannot be performed with the throughput required for primary screening of small molecules, and instead are most appropriate for validating compound mode of action. Thus, there is an urgent need for an HTS assay that can report on the binding of mutant ABD proteins to actin. Here we report our development of a fluorescence resonant energy transfer (FRET) assay that detects the binding of the mutant β-III-spectrin L253P ABD to F-actin in cultured mammalian cells. We further demonstrated the feasibility of this assay for HTS using the 1280-compound library of pharmacologically active compounds (LOPAC) in 1536 well plates.

2. Materials and Methods 2.1 Compound Handling and Preparation of 1536-Well Assay Plates.

The LOPAC compounds (Sigma-Aldrich, Mo., USA) were received in 96-well plates and reformatted into 384-well polypropylene intermediate plates (Greiner Bio-One, Kremsmunster, Austria) using a multichannel liquid handler, BioMek FX (Beckman Coulter, Miami, Fla., USA), then transferred to 384-well Echo Qualified source-plates (Labcyte Inc, Sunnyvale, Calif., USA). Assay plates were prepared by transferring 5 nL of the 10 mM compound stocks in columns 3-22 and 27-46 or DMSO in columns 1-2, 23-26 and 47-48 from the source plates to 1536-well black polypropylene plates (Greiner), using an Echo 550 acoustic dispenser (Labcyte Inc.). These assay plates were then heat-sealed using a PlateLoc Thermal Microplate Sealer (Agilent Tech., Santa Clara, Calif., USA) and stored at −20° C. prior to usage. Swinholide A was purchased from Cayman Chemical (Ann Arbor, Mich., USA).

2.2. Molecular Biology.

The GFP-ABD DNA was constructed with GFP sequence genetically fused to N-terminus of the L252P β-III-spectrin (human) ABD residues 1-284. The Lifeact-mCherry DNA was a gift from Michael Davidson (Addgene plasmid #54491), and contains mCherry genetically fused to the C-terminus of Lifeact. For expression in HEK293-6E cells (National Research Council Canada; Ottawa, Canada), DNA sequences were subcloned into pTT5 vector (National Research Council Canada; Ottawa, Canada) using NheI-HF and NgoMIV restriction enzyme sites. For expression in *E. coli*, the L253P β-III-spectrin ABD and Lifeact-mCherry DNA sequences were sub-cloned into the BsaI site in the vector pE-SUMOpro (LifeSensors), using AarI and XbaI.

2.3 Cell Culture.

At 2×10$^6$ cells/mL, HEK293-6E cells were transfected with GFP-ABD (2.4 µg), Lifeact-mCherry (2.4-16.8 µg), mCherry (1.2-16.8 µg), and/or pTT5 (0.8-17.6 µg) using the 293fectin protocol (Thermo Fisher Scientific) with 20 µg total DNA. The cells were harvested 24 hours later by centrifugation at 100×g for 5 min, and then washed twice with PBS. Cell viability and concentration were determined using trypan blue assay and a Countess cell counter (Invitrogen).

2.4 HTS Cell Preparation and FRET Measurements.

Using a Multidrop Combi liquid dispenser (Thermo Fisher Scientific), 10$^6$ cells/mL were dispersed into 1536-well and 384-well plates as 5 or 50 µL aliquots, respectively. For control and tool compound plates, 100 nL of DMSO or potential tool compound was loaded using the Mantis (Formulatrix). For follow-up retesting of purchased LOPAC screen hits, 384 well plates were loaded with 1 µL compound using a Mosquito LV (SPTLabTech, United Kingdom). Two to three hours after sample loading, fluorescence lifetime measurements were performed using high-throughput fluorescence plate-readers provided by Photonic Pharma LLC (MN, USA), including one detecting fluorescence lifetime and another detecting fluorescence spectra, as described previously [14-17].

2.6 HTS Data Analysis

Time-resolved fluorescence waveforms for each well were fitted based on a one-exponential decay function using least-squares minimization global-analysis software, as detailed previously [16]. The FRET efficiency (E) was determined as the fractional decrease of donor fluorescence lifetime ($\tau_D$), due to the presence of acceptor fluorophore ($\tau_{DA}$), using the following equation:

$$E = 1 - \frac{\tau_{DA}}{\tau_D}$$

Assay quality was determined based on FRET assay samples in wells pre-loaded with control (DMSO) and tested tool compound, as indexed by the Z' factor:

$$Z' = 1 - 3\frac{\sigma_{DMSO} + \sigma_{Tool}}{|\mu_{DMSO} - \mu_{Tool}|}$$

where $\sigma_{DMSO}$ and $\sigma_{Tool}$ are the SDs of the DMSO $\tau_{DA}$ and tool compound $\tau_{DA}$, respectively; $\mu_{DMSO}$ and $\mu_{Tool}$ are the means of the DMSO $\tau_{DA}$ and tool compound $\tau_{DA}$, respectively. A compound was considered a Hit if it changed $\tau_{DA}$ by >4SD relative to that of control $\tau_{DA}$ that were exposed to 0.1% DMSO.

2.7. Protein Preparation

Actin was purified from acetone powder derived from the psoas muscle of New Zealand white rabbit (*Oryctolagus cuniculus*) [18]. Filamentous (F)-actin was stored for up to 3 days on ice before use in binding assays. Within an hour of the binding assay, the F-actin was clarified at 100,000×g at 4° C. for 10 min prior to setting up binding assays. The L253P β-III-spectrin ABD was expressed in *E. coli* BL21 (DE3) (Novagen). The ABD was purified and the His-SUMO tag proteolytically removed, as previously described [19], except size-exclusion chromatography was not performed due to the high purity of the ABD protein. Lifeact-mCherry protein was similarly prepared. A Bradford assay was performed to determine clarified F-actin and ABD protein concentrations.

2.8. F-Actin Co-Sedimentation Assays

F-actin and ABD binding assays were performed as previously described [10]. In brief, binding assays used 1 µM ABD protein, 1 µM F-actin and 1-50 µM compound (as indicated) or DMSO control for a total reaction volume of 60 µL in F-buffer containing 10 mM Tris, pH 7.5, 150 mM NaCl, 0.5 mM ATP, 2 mM MgCl$_2$, and 1 mM DTT. Following 30 min incubation at room temperature (21° C.). F-actin was pelleted using centrifugation at 100,000×g at 25° C. for 30 min. Unbound ABD in the supernatant was measured following SDS-PAGE and Coomassie blue staining in accord [10]. In addition, control co-sedimentations assays that lacked actin were performed to test if compounds cause ABD aggregation. F-actin and Lifeact-mCherry binding assays were undertaken with 2 µM Lifeact-mCherry, 30 µM F-actin and 1-50 µM compound (as indicated) or DMSO control for a total reaction volume of 80 µL in F-buffer. For a no-actin binding control, an assay sample with no F-actin was also set up. Binding reactions were allowed to reach equilibrium at room temperature (21° C.) for 30 min and then F-actin was pelleted by centrifugation at 100,000×g at 25° C. for 30 min. The amount of unbound Lifeact-mCherry was sampled by loading 7 µL of spin supernatant on a low volume black bottom 384-well plate (Greiner). Amount of mCherry was determined by acquiring fluorescence spectrum peak intensity at ~600 nm using a spectral unmixing plate reader (Fluorescence Innovations, Inc) equipped with a 532 nm laser (Laserglow Technologies, Ontario, Canada) for excitation, 532 nm longpass filter for emission, and PMT for emission detection. The fraction of Lifeact-mCherry bound to F-actin was determined by subtracting from one the fraction of supernatant fluorescence intensity relative to the no-actin control sample, using the following equation:

$$\text{Fraction of Lifeact bound} = 1 - \frac{F_{compound/DMSO}}{F_{No-actin}}.$$

Where $F_{control/DMSO}$ is the peak mCherry fluorescence of assay samples containing compound or DMSO control, and $F_{no-actin}$ is the peak mCherry fluorescence of assay samples that contained no F-actin.

2.9 Trypan Blue Cell Viability Assays

HEK293-6E cell viability was measured using trypan blue (0.03%) staining and a Countess Automated Cell counter (Invitrogen). Non-transfected HEK293-6E cells were spun at 100×g for 5 min at 21° C., and resuspended in 10 mL of PBS. The centrifugation and resuspension were repeated twice more. Final cell concentration was 1×10$^6$ cells/mL. Cells were incubated with 2% DMSO, or 3-50 µM compound (as indicated) for 3 hrs at room temperature (21° C.). After addition of 100 µL of 0.06% trypan blue solution in PBS, 10 µL was loaded on a slide and injected into the cell counter, and cell viability was measured.

2.10 Analysis and Presentation of Data.

Data is presented as mean±SD or ±SEM, as indicated. For statistical difference determination, unpaired Student's T-test or one-way ANOVA followed by Tukey's post-hoc test was performed, as indicated. Statistical analyses were performed with GraphPad Prism and Origin. Significance was accepted at P<0.05. EC50 values were derived from fits to Hill equations.

3. Results 3.1 Biosensor Development and Tool Compound Characterization.

To develop a biosensor that monitors the binding of mutant L253P β-III-spectrin to actin filaments in live cells, a fluorescence resonance energy transfer (FRET) approach was tested. A FRET donor construct consisting of green fluorescent protein fused to the N-terminus of the mutant ABD (GFP-ABD-L253P) was co-expressed in HEK293-ENAB1-6E (HEK293-6E) cells with a FRET acceptor construct consisting of the actin-binding peptide, Lifeact, fused to the N-terminus of red fluorescent protein, mCherry (Lifeact-mCherry). Lifeact is a 17 amino acid peptide derived from the yeast actin-binding protein ABP140 [21]. The Lifeact-mCherry fusion protein binds specifically to actin filaments (Kd=13.2 µM) [22], with negligible affinity for actin monomers. Although the Lifeact binding site is unknown on actin, we predict that it overlaps with the myosin binding site given the reported ability of myosin to inhibit binding of ABP140 to actin [23], and the similarity in the actin-binding sequences of Lifeact and myosin (FIG. 1). Based on the known position of ABD on actin, we predicted distances of 51 and 79 Å between GFP and mCherry, depending on which neighboring actin unit Lifeact-mCherry is bound (FIG. 1). With a known Förster distance of 52.4 Å [24], this equates to FRET values of 0.54 and 0.08, respectively, which should yield a strong biosensor platform. To design a system most compatible for large production and eventual screening of 50,000+compound libraries, we used HEK293-6E cells, which is a suspension cell line that yields greater levels (>3-fold) of recombinant protein expression [25,26]. With constant amount of GFP-ABD-L253P expressed, increased Lifeact-mCherry expression increases FRET with an exponential plateau to 0.12 (FIG. 2a). To measure the non-specific component to our FRET readout, we concurrently tested expression of mCherry in place of Lifeact-mCherry. The calculated FRET in our control mCherry cells demonstrates an increase in non-specific FRET with increasing expression of mCherry, although in a linear fashion (FIG. 2a). With the trade-off between high FRET and minimal non-specific FRET, the donor to acceptor ratio 1:2 was chosen for the experiments that followed (FIG. 2a). Cell lysis by addition of 0.1% Triton X-100 abolished both total FRET (GFP-ABD-L253P and Lifeact-mCherry co-expression) and non-specific FRET (GFP-ABD-L253P and mCherry co-expression), suggesting that our FRET readout may be responsive to compounds that alter cell viability, and not singularly to compounds altering ABD-actin binding. We proceeded to test the compatibility of the GFP-ABD-L253P and Lifeact-mCherry assay for primary compound screening, and the GFP-ABD-L253P and mCherry assay as a potential high-throughput counter screen.

Figure 2:
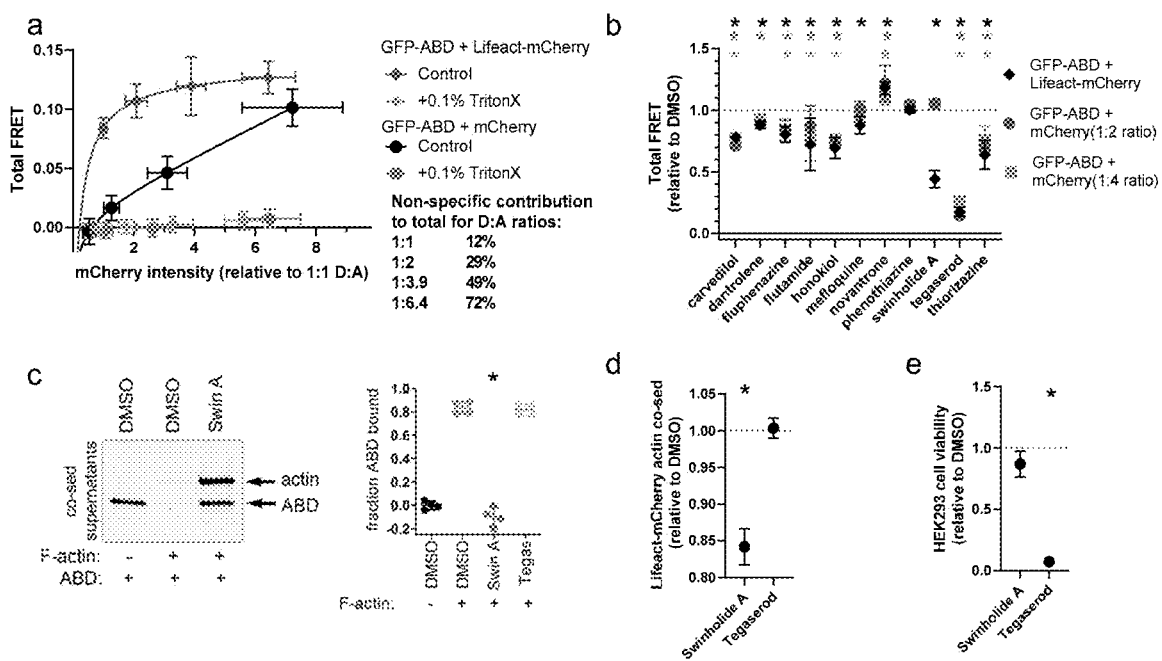
FIG. 2 shows measuring specific FRET and identifying potential tool compound, swinholide A, using suspension cells.

To identify a potential positive control tool compound for our FRET assay, we tested the effect of a range of actin-binding compounds [17,27] on our FRET readouts. As shown in FIG. 2b, most actin-binding compounds significantly shift our GFP-ABD-L253P and Lifeact-mCherry co-expression (primary) FRET readout. Notably, both 1 µM swinholide A and 50 µM tegasarod reduced total FRET by >50% in our primary FRET assay, suggesting these may be useful tool compounds (FIG. 2b). However, tegasarod, as observed for most of the actin-binding compounds, exhibited a similar impact on the counter FRET assay samples (FIG. 2b). This suggests that tegaserod reduces the primary FRET readout by an indirect mechanism such as compound fluorescence or cytotoxicity. Indeed, addition of tegasarod did not alter actin-binding of ABD (FIG. 2c) nor Lifeact (FIG. 2d) in co-sedimentation assays, but greatly diminished cell viability (FIG. 2e) in trypan blue assays. This suggests that the tegaserod-induced 83% FRET reduction is due to cell lysis, given the 92% decrease in cell viability (FIG. 2). In contrast, swinholide A did not significantly alter the counter FRET readout (FIG. 4 FIG. 2b), nor cell viability (FIG. 2e), but did reduce ABD and Lifeact binding to F-actin, as indicated by the shift in ABD and Lifeact-mCherry from co-sedimentation sample actin pellets to supernatants (FIGS. 2c and d). These data suggest that swinholide A is an ideal tool compound to evaluate the primary FRET assay for HTS.

Figure 3:
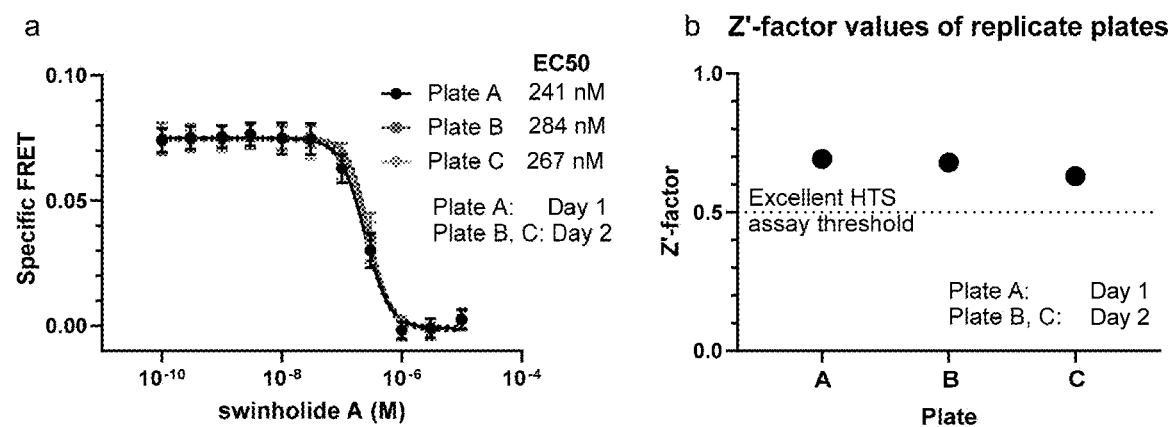
FIG. 3 shows swinholide A is a reproducible, positive control tool compound for FRET assays in 1536 well plates.

To evaluate the quality of the assay, we used the tool compound, swinholide A, to determine assay robustness and reproducibility. Triplicate, 12-point concentration response curves (0.01 and 30 µM versus DMSO-only; 12 points, half log), show that swinholide A reduces FRET in a dose responsive manner, with an average EC50 value of 264 nM (FIG. 3a). This is in the range of previously reported affinity value in an actin sedimentation assay (50 nM) [28]. To gauge HTS assay robustness, we used swinholide A to measure the Z' value, which is a measure of the signal window and data variation between control and tool compound effect. Classically, a value of $0.5 \leq Z' < 1$ indicates an excellent assay that is ready for large-scale HTS [29]. Using 1536-well plates containing half swinholide A and half DMSO negative control, an average Z'-factor of 0.67 was calculated (FIG. 3b), which surpasses the 0.5 Z'-factor excellence threshold. Significantly, Z' and EC50 values were highly reproducible when measured in repeat tests performed within the same day, or on different days, using different batches of transfected cells (FIG. 3). These results indicated compatibility of the assay for HTS.

3.2. HTS Performance

To test the performance of the assay in HTS, the 1280 library of pharmacologically active compounds (LOPAC), together with 256 DMSO controls, were dispensed in 5 nL volumes into individual wells of 1536-well microplates and stored at −20° C. until use. To test the reproducibility of replicate screens in the same day, a single batch of HEK293 cells was transfected with GFP-ABD-L253P and Lifeact-mCherry. In addition, control cells were transfected with only GFP-ABD-L253P, to determine compound effect on donor-only lifetime ($\tau_D$). To test reproducibility of the screens across different days, identical transfections were performed on another batch of HEK293-6E cells on a second day. Following plate thaw, 5 µL of assay cells were loaded in each well via a Multi-drop liquid dispenser, and a time course of compound effects at 20, 120, and 180 min post load on fluorescence lifetime was acquired using a fluorescence lifetime plate reader (FLT-PR). This technology has been advanced to high density 1536-well plates in recent years for successful HTS using a range of protein biosensors including sarco/endoplasmic reticulum Ca-ATPase [14,15,30,31], ryanodine receptor [29,32], actin [17], tumor necrosis factor receptor 1 [33,34], tau [35]. Fluorescent interfering compounds were identified as compounds that altered $\tau_D$ FLT by >3 standard deviation (SD) threshold, and or, altered the fluorescence spectrum by >3SD, as previously described [14-16,29,32]. As shown by representative data in FIG. 4a-b, several interfering compounds dramatically overshadow the impact of non-interfering Hits. In particular, FIG. 4a appears to suggest that compound effect on FRET is lowered over time. However, removal of interfering compounds, shown in FIG. 4a, visibly indicates that Hit compound effects are enhanced over time. Indeed, the overall Hit rates generally increased between 20 and 120 min (Table 1 and Table 2). Given that 120 min incubation yields the highest Hit rate values in all plates, all FRET data from this point onward refers to data acquired 120 min following compound loading.

Figure 8:
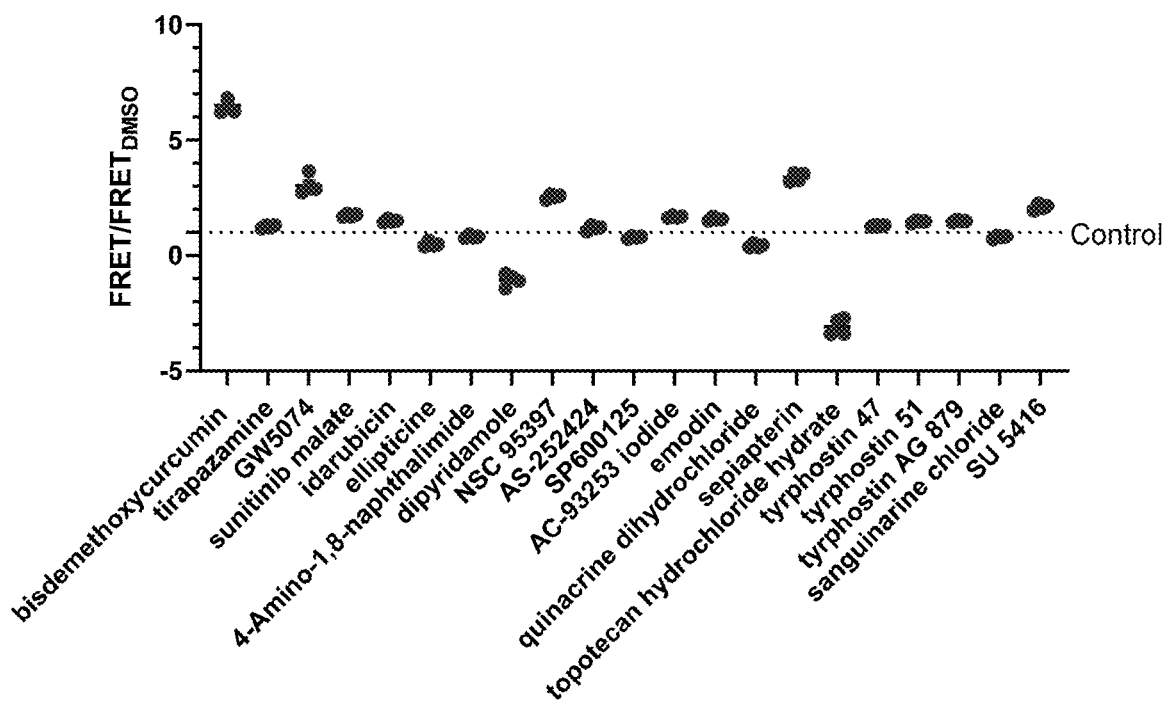
FIG. 8 shows interfering compounds identified as Hits by ABD-Lifeact FRET assay using the library of pharmacologically active compounds in 1536-well plates. Relative FRET effect of LOPAC Hits that were identified (with 4SD threshold) in at least 2 of the 4 screens, and confirmed as fluorescently interfering compounds by spectral readout, as previously described (Schaaf et al., Biosensors (Basel) 2018, 8, doi:10.3390/bios8040099; Schaaf et al., SLAS Discov 2017, 22, 262-273, doi:10.1177/1087057116680151; Schaaf et al., SLAS Discov 2017, 22, 250-261, doi:10.1177/1087057116679637; Rebbeck et al., Sci Rep 2020, 10, 1791, doi:10.1038/s41598-020-58461-1; Rebbeck et al., SLAS Discov 2017, 22, 176-186, doi:10.1177/1087057116674312). n=4, data shown as mean±SEM.

For an acceptable Hit rate (0.5%-3%) [36], we adopted a 4 SD threshold for Hits, which yielded a Hit rate range of 2-3.2% (Table 1), compared to the 3.8-5.4% and 1.6-2% for 3 SD and 5 SD thresholds, respectively (Table 2). At the 4 SD threshold, compounds that were identified as Hits in one screen typically repeated as Hits in replicate screens. As shown in Table 1, the reproducibility of Hit compounds in more than 1, 2 and 3 screens is 82.0±2.8%, 68.6±6.0% and 64.1±6.1%, respectively. Furthermore, there is little variability in the magnitude of FRET change induced by compounds that were identified in at least 2 of the 4 screens (FIG. 4c and FIG. 8). Of the 11 Hits, two compounds increased FRET, and nine compounds decreased FRET (FIG. 4c). Notably, none of these Hit compounds are classically known to bind to actin, Lifeact, nor the β-III-spectrin ABD. Because our ultimate interest is to identify compounds that reduce the aberrant affinity of mutant β-III-spectrin for actin, we further characterized the nine hits that reduced FRET.

TABLE 1

Number (#) of Hits and Hit reproducibility for 4 standard deviation (SD) threshold

| | LOPAC Day 1 Plate 1 | LOPAC Day 1 Plate 2 | LOPAC Day 2 Plate 1 | LOPAC Day 2 Plate 2 |
| --- | --- | --- | --- | --- |
| # of Hits 20 min (hit rate %) | 18 (1.4%) | 23 (1.8%) | 28 (2.2%) | 26 (2%) |
| # of Hits 120 min (hit rate %) | 26 (2%) | 34 (2.7%) | 41 (3.2%) | 32 (2.5%) |

TABLE 1-continued

Number (#) of Hits and Hit reproducibility for 4 standard deviation (SD) threshold

|  | LOPAC Day 1 Plate 1 | LOPAC Day 1 Plate 2 | LOPAC Day 2 Plate 1 | LOPAC Day 2 Plate 2 |
|---|---|---|---|---|
| # of Hits 180 min (hit rate %) | 26 (2%) | 26 (2%) | 33 (2.6%) | 25 (2%) |
| % of Repeated Hits in 2 plates[1] | 88.5% | 79.4% | 75.6% | 84.4% |
| % of Repeated Hits in 3 plates[1] | 84.6% | 64.7% | 56.1% | 68.8% |
| % of Repeated Hits in 4 plates[1] | 80.8% | 61.8% | 51.2% | 62.5% |

[1]Data for 120 min incubation.

TABLE 2

Number (#) of Hits and Hit reproducibility for 3 and 5 standard deviation (SD) thresholds.

|  |  | LOPAC Day 1 Plate 1 | LOPAC Day 1 Plate 2 | LOPAC Day 2 Plate 1 | LOPAC Day 2 Plate 2 |
|---|---|---|---|---|---|
| 3SD | # of Hits 20 min (hit rate %) | 28 (2.2%) | 38 (3%) | 40 (3.1%) | 41 (3.2%) |
|  | # of Hits 120 min (hit rate %) | 49 (3.8%) | 56 (4.4%) | 69 (5.4%) | 64 (5%) |
|  | # of Hits 180 min (hit rate %) | 49 (3.8%) | 44 (3.4%) | 63 (4.9%) | 50 (3.9%) |
|  | % of Repeated Hits in 2 plates[1] | 77.6% | 73.2% | 63.8% | 62.5% |
|  | % of Repeated Hits in 3 plates[1] | 71.4% | 66.1% | 55.1% | 54.7% |
|  | % of Repeated Hits in 4 plates[1] | 57.1% | 50% | 40.6% | 43.8% |
| 5SD | # of Hits 20 min (hit rate %) | 15 (1.2%) | 17 (1.3%) | 27 (2.1%) | 21 (1.6%) |
|  | # of Hits 120 min (hit rate %) | 21 (1.6%) | 22 (1.7%) | 26 (2%) | 25 (2%) |
|  | # of Hits 180 min (hit rate %) | 18 (1.4%) | 19 (1.5%) | 27 (2.1%) | 23 (1.8%) |
|  | % of Repeated Hits in 2 plates[1] | 90.5% | 95.5% | 88.5% | 88% |
|  | % of Repeated Hits in 3 plates[1] | 90.5% | 90.9% | 76.9% | 80% |
|  | % of Repeated Hits in 4 plates[1] | 90.5% | 86.4% | 73.1% | 76% |

[1]Data for 120 min incubation.

3.3 FRET Dose-Response Assay

Figure 4:
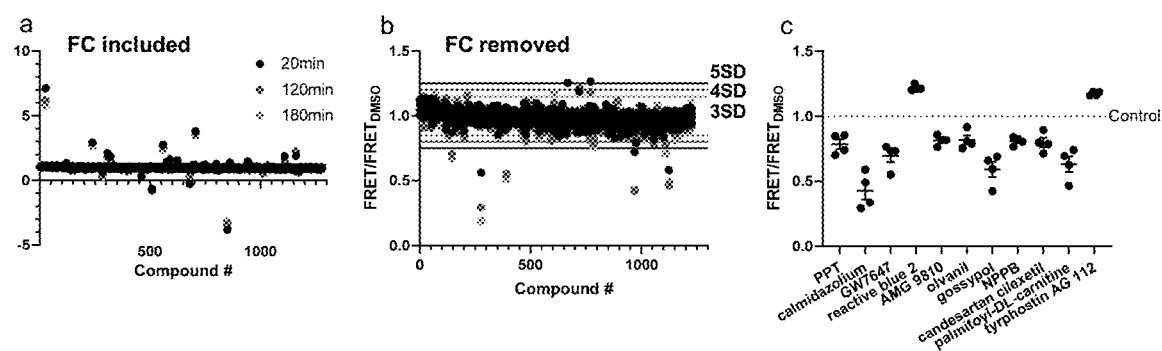
FIG. 4 shows HTS performance validation of ABD-Lifeact FRET assay using the library of pharmacologically active compounds in 1536-well plates.
Figure 5:
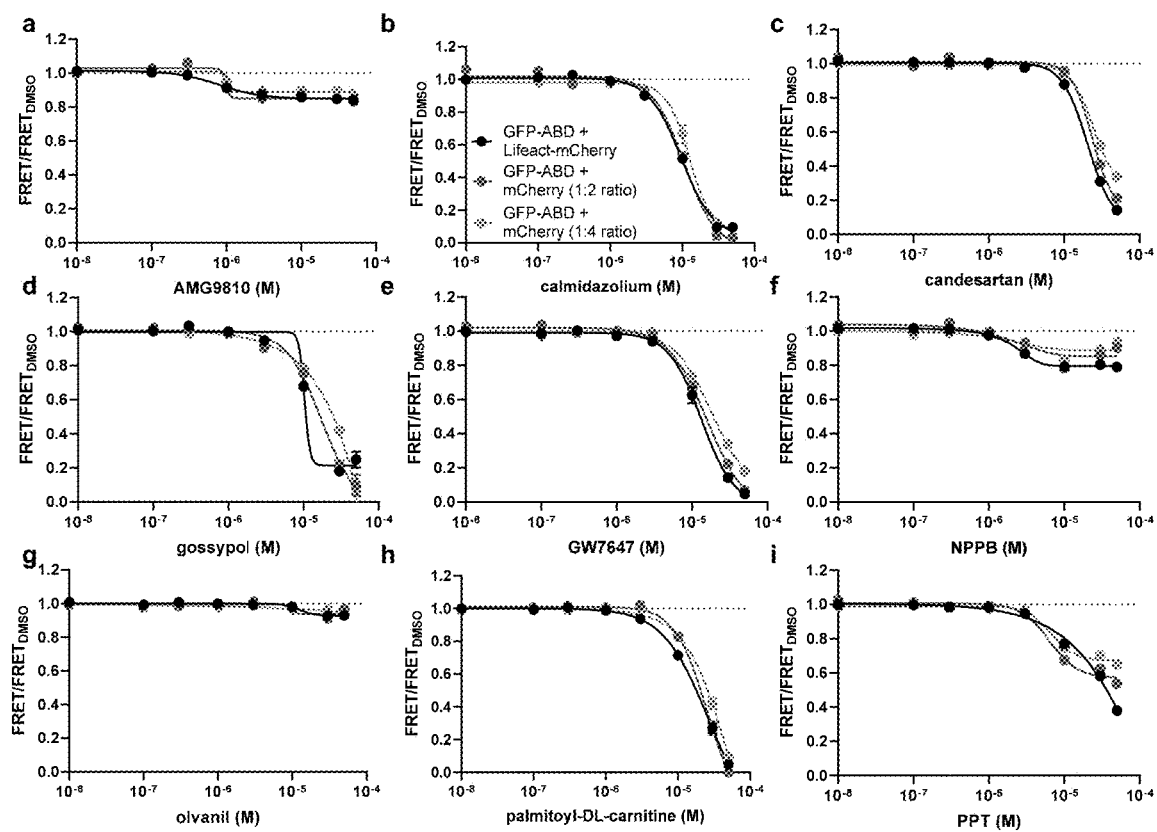
FIG. 5 shows FRET dose response of Hit compounds that decrease FRET. Dose response of Hit compounds (FIG. 5a) AMG 9810, (FIG. 5b) calmidazolium, (FIG. 5c) candesartan, (FIG. 5d) gossypol, (FIG. 5e) GW7647, (FIG. 5f) NPPB, (FIG. 5g) olvanil, (FIG. 5h) palmitoyl-DL-carnitine and (FIG. 5i) PPT were tested on the primary screen (GFP-ABD-L253P to Lifeact-mCherry FRET; 1:2 ratio) and two counter screens (GFP-ABD-L253P to mCherry non-specific FRET; 1:2 and 1:4 ratios). Data shown as mean±SEM, n=3.

To determine the dose-response relationships, we measured the FRET response to a range of Hit compound concentrations under the same assay conditions as used in the primary screen. Further, we also tested how Hit compounds altered FRET in our counter screen (GFP-ABD-L253P and mCherry). All nine repurchased compounds decreased counter FRET to similar levels observed in the primary screen (FIG. 4 and FIG. 5). This indicates that our Hit threshold in the primary screen is sufficient to identify FRET effectors. Curiously, all compounds displayed similar effects on counter screen FRET, suggesting that these compounds alter fluorescence, cell viability or protein aggregation.

3.4 Characterization of Hit Compound Mode of Action

To gain insight into Hit compound mode of action, we investigated the impact of compounds on co-sedimentation of ABD and Lifeact with actin, cell viability and ABD aggregation. calmidazolium, GW7647, NPPB and palmitoyl-DL-carnitine decreased actin-Lifeact co-sedimentation, suggesting that these compounds promote Lifeact dissociation from actin (FIG. 6a). However, this does not explain the impact of these compounds on the counter screens. Like tegaserod, screen Hits GW7647, palmitoyl-DL-carnitine and calmidazolium dramatically reduced cell viability (FIG. 6b), which would account for compound effect on both the primary and counter screen assays. Indeed, both calmidazolium and palmitoyl-DL-carnitine have been reported to reduce cell viability in mammalian cells [37,38]. Notably, olvanil, gossypol and candesartan cilexetil have also been previously found to reduce cell viability, though the impact was minimal (<10%) at the concentration (10 µM) used in this study, and greater with ≥10 µM compound [39-41]. With consensus between our findings and the literature on the impact of calmidazolium and pamitoyl-DL-carnitine on cell viability, we did not investigate the impact of these compounds further.

Figure 6:
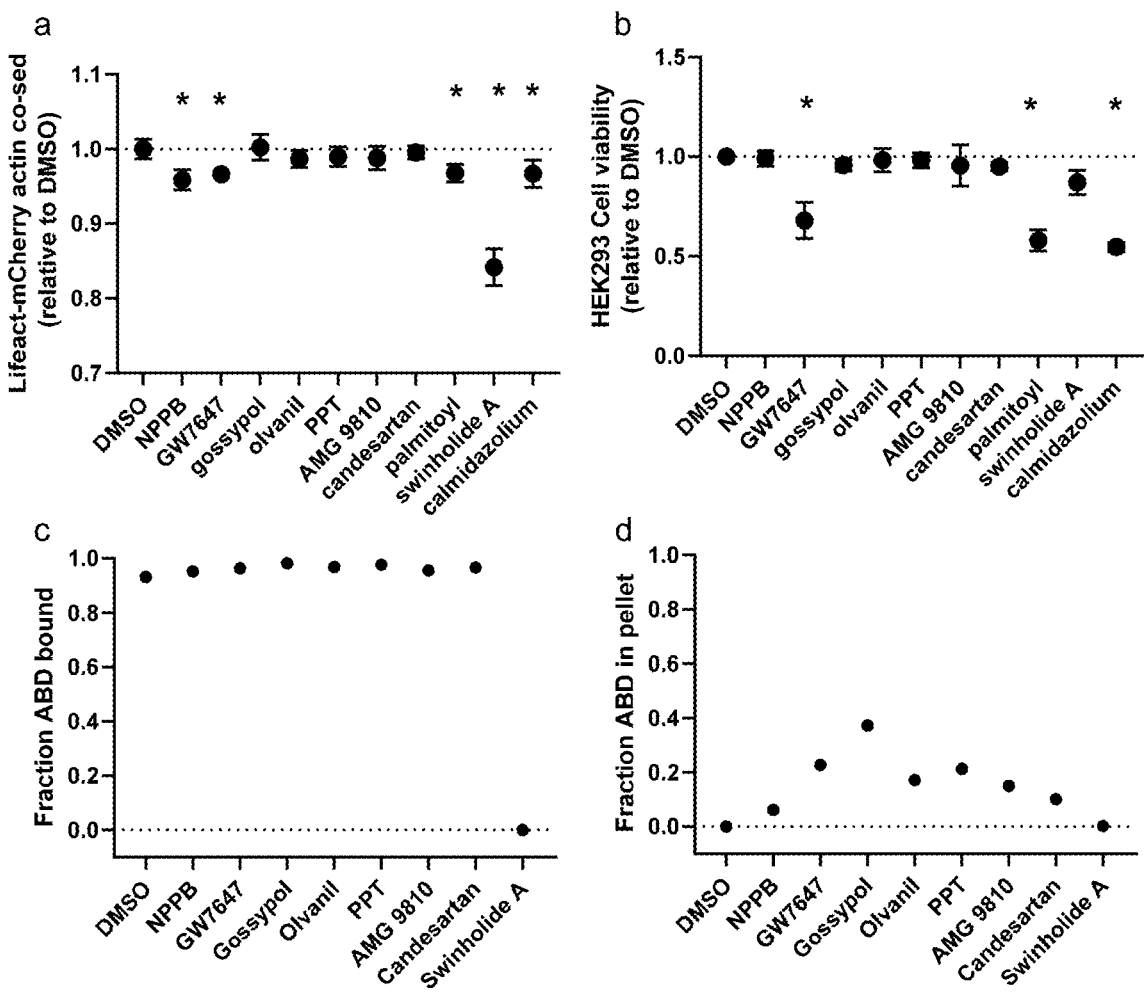
FIG. 6 shows FRET Hit mode of action evaluated using Lifeact-mCherry binding to actin, cell viability, ABD-L253P binding to actin, and ABD-L253P aggregation.

Similar to tegasarod, the remaining Hit compounds did not significantly reduce ABD-L253P to actin co-sedimentation (FIG. 6c). This further supports the quality of the counter screen, as all compounds that impacted the counter screen did not impact ABD-actin binding (FIG. 2, FIG. 5, FIG. 6). In addition to a reduction in cell viability, the primary and counter screen may be sensitive to compounds that promote ABD-L253P protein aggregation. Indeed, using the aggregator advisor database and tool [42], we identified gossypol, PPT and candesartan as known protein aggregators [43-45], and AMG 9810 as having 71% structural similarity with a known aggregator [43]. Our ABD-L253P to actin co-sedimentation assay is unlikely to be sensitive to ABD aggregation, as it is set up to monitor maximal sedimentation of ABD-L253P with actin at ~90% ABD-L253P co-sedimenting. To directly measure the impact of 10 µM Hit compounds on ABD aggregation, we repeated the ABD-actin co-sedimentation without actin present. As shown in FIG. 6d, the presence of 10 µM NBBP, GW7647, gossypol, olvanil, PPT, AMG 9810 or candesartan increases ABD pelleting during centrifugation, presumably due to protein aggregation. As to be expected, 1.6 µM swinholide A treatment does not alter ABD sedimentation without the presence of actin (FIG. 6d). Overall, our data suggests that the counter screen is sensitive to compounds that are detected in our primary screen due to ABD protein aggregation and or cytotoxicity.

4. Discussion

For HTS, we developed a highly quantitative time-resolved FRET assay that reports on the elevated actin affinity induced by the L253P spinocerebellar ataxia type 5 (SCA5) mutation in β-spectrin. This live cell assay is based on the formation of a ternary complex consisting of GFP-ABD-L253P, Lifeact-mCherry, and actin. Treatment of cells with the F-actin severing compound, swinholide A, strongly reduced FRET, thus demonstrating the requirement of F-actin to assemble the ternary complex that brings GFP-ABD and Lifeact-mCherry into close proximity with each other. Following assay optimization in HEK293-6E suspension cells and 1536-well microplates, we showed using a high-throughput fluorescence lifetime plate reader [15,32,34], that the assay is robust based on high Z' scores (>0.5) using 1536-well plates containing half DMSO and half swinholide A, and is reproducible based on high repeatability of Hits in replicate screens of the 1280-compound LOPAC library. Moving forward, our goal is to apply the optimized assay and protocols reported here to screen larger libraries with greater diversity in molecular scaffolds to identify small molecules that directly bind the mutant ABD and reduce its affinity for actin. The challenge will be to identify compounds that modulate the actin-binding affinity of mutant β-III-spectrin into the 'Goldilocks' zone—a zone where aberrant binding is sufficiently suppressed to prevent disease progression while allowing adequate binding to support proper cell function. A similar strategy of pulsed-drug dosing has proven effective in treating diseases like leukemia and melanoma where the oncogenic factor is known to impinge on multiple biological pathways [46].

In addition to the primary high-throughput FRET assay described above, we also developed a high-throughput counter assay to remove Hits that impact the primary FRET assay through undesired modes of action. The counter assay is based on an intermolecular FRET signal measured in cells expressing GFP-ABD-L253P and mCherry. We showed that this "non-specific" intermolecular FRET signal is sensitive to cell lysis, as observed following Triton X-100 or tegaserod treatment (FIG. 2). The counter assay was further validated by Hits identified in our primary screens of the LOPAC library. All nine Hits that lowered FRET in our primary assay (GFP-ABD-L253P and Lifeact-mCherry), had a similar impact on FRET in the counter assay. Our secondary assay showed that the Hit compounds decreased FRET likely by inducing cytotoxicity or ABD aggregation. The counter assay should also be sensitive to compounds that impact FRET due to intrinsic fluorescence. The 1:4 ratio GFP-ABD:mCherry expression ratio in the counter assay can be employed due to greater signal window, and because this ratio appears to reflect the same compound impacts as the 1:2 ratio with smaller signal window. Because of the sensitivity of the counter assay and the ability to perform it with high-throughput, it is possible that a higher hit rate can be accommodated in the primary screen by lowering the Hit threshold from 4 SD to 3 SD. Based on LOPAC screening this would increase the overall Hit rate from 2-3.2% to 3.8-5.4%. Notably, ~65% of Hits would likely be eliminated as fluorescent compounds before progressing to cherry picking, which is the process of directly selecting compounds from the same master plates used for setting up the library assay plates. The lower threshold would allow the identification of Hits that have a smaller impact on binding of the mutant ABD to actin, and increase the probability of identifying Hit compounds with the desired mode of action.

Figure 7:
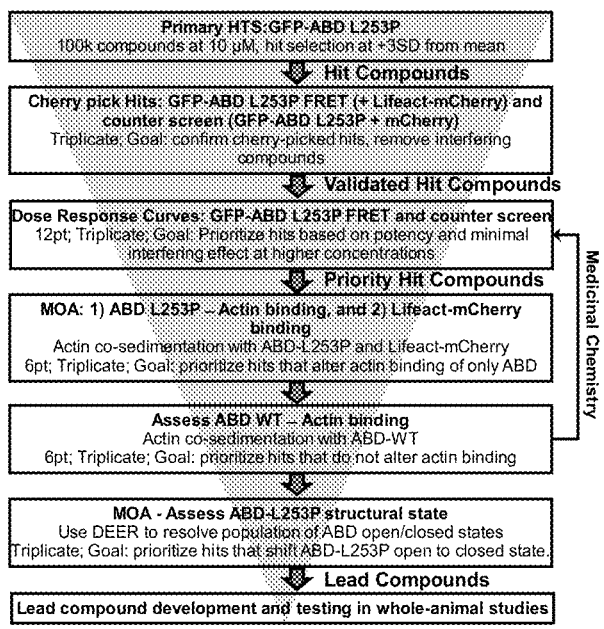
FIG. 7 shows proposed ABD L253P HTS Platform for drug screening and development starting with a 100,000 compound library screen.

Our primary and counter screens will yield a pool of Hits enriched with compounds that disrupt the ternary FRET complex, and can be further evaluated for their mode of action in secondary assays. As performed here, in vitro co-sedimentation assays can resolve if these compounds act directly on the mutant ABD, as desired, or actin. Specifically, we anticipate that compounds that bind to actin will alter Lifeact-mCherry to actin co-sedimentation, similar to the impact on ABD-L253P to actin co-sedimentation. Transient phosphorescence anisotropy can be performed to identify and eliminate compounds impacting actin structural dynamics [17,18,47,48], if we choose to pursue a compound that alters Lifeact-mCherry co-sedimentation with actin. Additional co-sedimentation assays with the wild-type β-III-spectrin ABD will allow selection of compounds that have greater affinity for the mutant ABD vs wild-type. We envision that some compounds that recognize the open conformation of the ABD will preferentially target the mutant ABD over wild-type, because the mutant populates the "open" conformation more significantly than wild-type. A flow chart of our screening strategy is given in FIG. 7.

The screening platform and protocols that we reported here have the potential to identify a molecular scaffold that can be further developed into a therapeutic for SCA5. Such a drug could be used to treat SCA5 patients carrying the L253P mutation, and potentially for the other SCA5-linked mutations located at the CH1-CH2 interface, that may also increase actin-binding [49]. Moreover, a drug developed for SCA5 may also be useful in other rare diseases, such as Focal Segmental Glomerulosclerosis, Congenital Macrothrombocytopenia, Otopalatiodigital Syndrome, Autosomal Dominant Atelosteogenesis, William's Distal Myopathy, which have also been linked to "gain-of-function" ABD mutations in spectrin-related proteins, including filamin [5-7], and α-actinin [2-4]. Alternatively, we expect that our FRET biosensor could easily be adapted to include the mutant filamin or α-actinin ABD, and screening performed as described in FIG. 7, to identify compounds specifically targeting the spectrin-related mutant ABDs. Our cell-based assay platform is versatile, and our validated screening protocols provide an inroad to drug discovery for spinocerebellar ataxia and numerous other actin-linked cytoskeletal disorders.

Citations for Example 1
1. Liu, L. Z.; Ren, M.; Li, M.; Ren, Y. T.; Sun, B.; Sun, X. S.; Chen, S. Y.; Li, S. Y.; Huang, X. S. A Novel Missense Mutation in the Spectrin Beta Nonerythrocytic 2 Gene Likely Associated with Spinocerebellar Ataxia Type 5. Chin Med J (Engl) 2016, 129, 2516-2517, doi:10.4103/0366-6999.191834.
2. Kaplan, J. M.; Kim, S. H.; North, K. N.; Rennke, H.; Correia, L. A.; Tong, H. Q.; Mathis, B. J.; Rodriguez-Perez, J. C.; Allen, P. G.; Beggs, A. H., et al. Mutations in ACTN4, encoding alpha-actinin-4, cause familial focal segmental glomerulosclerosis. Nat Genet 2000, 24, 251-256, doi:10.1038/73456.
3. Weins, A.; Kenlan, P.; Herbert, S.; Le, T. C.; Villegas, I.; Kaplan, B. S.; Appel, G. B.; Pollak, M. R. Mutational and Biological Analysis of alpha-actinin-4 in focal segmental glomerulosclerosis. J Am Soc Nephrol 2005, 16, 3694-3701, doi:10.1681/ASN.2005070706.
4. Murphy, A. C.; Lindsay, A. J.; McCaffrey, M. W.; Djinovic-Carugo, K.; Young, P. W. Congenital macrothrombocytopenia-linked mutations in the actin-binding domain of alpha-actinin-1 enhance F-actin association. FEBS Lett 2016, 590, 685-695, doi:10.1002/1873-3468.12101.
5. Clark, A. R.; Sawyer, G. M.; Robertson, S. P.; Sutherland-Smith, A. J. Skeletal dysplasias due to filamin A mutations result from a gain-of-function mechanism distinct from allelic neurological disorders. Hum Mol Genet 2009, 18, 4791-4800, doi:10.1093/hmg/ddp442.
6. Sawyer, G. M.; Clark, A. R.; Robertson, S. P.; Sutherland-Smith, A. J. Disease-associated substitutions in the filamin B actin binding domain confer enhanced actin binding affinity in the absence of major structural disturbance: Insights from the crystal structures of filamin B actin binding domains. *J Mol Biol* 2009, 390, 1030-1047, doi:10.1016/j.jmb.2009.06.009.

7. Duff, R. M.; Tay, V.; Hackman, P.; Ravenscroft, G.; McLean, C.; Kennedy, P.; Steinbach, A.; Schoffler, W.; van der Ven, P. F. M.; Furst, D. O., et al. Mutations in the N-terminal actin-binding domain of filamin C cause a distal myopathy. *Am J Hum Genet* 2011, 88, 729-740, doi:10.1016/j.ajhg.2011.04.021.

8. Henderson, D. M.; Lee, A.; Ervasti, J. M. Disease-causing missense mutations in actin binding domain 1 of dystrophin induce thermodynamic instability and protein aggregation. *Proc Natl Acad Sci USA* 2010, 107, 9632-9637, doi:10.1073/pnas.1001517107.

9. Ohara, O.; Ohara, R.; Yamakawa, H.; Nakajima, D.; Nakayama, M. Characterization of a new beta-spectrin gene which is predominantly expressed in brain. *Brain Res Mol Brain Res* 1998, 57, 181-192.

10. Avery, A. W.; Crain, J.; Thomas, D. D.; Hays, T. S. A human beta-III-spectrin spinocerebellar ataxia type 5 mutation causes high-affinity F-actin binding. *Sci Rep* 2016, 6, 21375, doi:10.1038/srep21375.

11. Burk, K.; Zuhlke, C.; Konig, I. R.; Ziegler, A.; Schwinger, E.; Globas, C.; Dichgans, J.; Hellenbroich, Y. Spinocerebellar ataxia type 5: clinical and molecular genetic features of a German kindred. *Neurology* 2004, 62, 327-329, doi:10.1212/01.wnl.0000103293.63340.c1.

12. Ikeda, Y.; Dick, K. A.; Weatherspoon, M. R.; Gincel, D.; Armbrust, K. R.; Dalton, J. C.; Stevanin, G.; Durr, A.; Zuhlke, C.; Burk, K., et al. Spectrin mutations cause spinocerebellar ataxia type 5. *Nat Genet* 2006, 38, 184-190, doi:10.1038/ng1728.

13. Avery, A. W.; Thomas, D. D.; Hays, T. S. beta-III-spectrin spinocerebellar ataxia type 5 mutation reveals a dominant cytoskeletal mechanism that underlies dendritic arborization. *Proc Natl Acad Sci USA* 2017, 114, E9376-E9385, doi:10.1073/pnas.1707108114.

14. Schaaf, T. M.; Li, A.; Grant, B. D.; Peterson, K.; Yuen, S.; Bawaskar, P.; Kleinboehl, E.; Li, J.; Thomas, D. D.; Gillispie, G. D. Red-Shifted FRET Biosensors for High-Throughput Fluorescence Lifetime Screening. *Biosensors (Basel)* 2018, 8, doi:10.3390/bios8040099.

15. Schaaf, T. M.; Peterson, K. C.; Grant, B. D.; Bawaskar, P.; Yuen, S.; Li, J.; Muretta, J. M.; Gillispie, G. D.; Thomas, D. D. High-Throughput Spectral and Lifetime-Based FRET Screening in Living Cells to Identify Small-Molecule Effectors of SERCA. *SLAS Discov* 2017, 22, 262-273, doi:10.1177/1087057116680151.

16. Schaaf, T. M.; Peterson, K. C.; Grant, B. D.; Thomas, D. D.; Gillispie, G. D. Spectral Unmixing Plate Reader: High-Throughput, High-Precision FRET Assays in Living Cells. *SLAS Discov* 2017, 22, 250-261, doi:10.1177/1087057116679637.

17. Guhathakurta, P.; Prochniewicz, E.; Grant, B. D.; Peterson, K. C.; Thomas, D. D. High-throughput screen, using time-resolved FRET, yields actin-binding compounds that modulate actin-myosin structure and function. *J. Biol Chem* 2018, 293, 12288-12298, doi:10.1074/jbc.RA118.002702.

18. Prochniewicz, E.; Zhang, Q.; Howard, E. C.; Thomas, D. D. Microsecond rotational dynamics of actin: spectroscopic detection and theoretical simulation. *J Mol Biol* 1996, 255, 446-457.

19. Avery, A. W.; Fealey, M. E.; Wang, F.; Orlova, A.; Thompson, A. R.; Thomas, D. D.; Hays, T. S.; Egelman, E. H. Structural basis for high-affinity actin binding revealed by a beta-III-spectrin SCA5 missense mutation. *Nat Commun* 2017, 8, 1350, doi:10.1038/s41467-017-01367-w.

20. Holmes, K. C.; Angert, I.; Kull, F. J.; Jahn, W.; Schroder, R. R. Electron cryo-microscopy shows how strong binding of myosin to actin releases nucleotide. *Nature* 2003, 425, 423-427, doi:10.1038/nature02005.

21. Riedl, J.; Crevenna, A. H.; Kessenbrock, K.; Yu, J. H.; Neukirchen, D.; Bista, M.; Bradke, F.; Jenne, D.; Holak, T. A.; Werb, Z., et al. Lifeact: a versatile marker to visualize F-actin. *Nat Methods* 2008, 5, 605-607, doi:10.1038/nmeth.1220.

22. Courtemanche, N.; Pollard, T. D.; Chen, Q. Avoiding artefacts when counting polymerized actin in live cells with LifeAct fused to fluorescent proteins. *Nat Cell Biol* 2016, 18, 676-683, doi:10.1038/ncb3351.

23. Asakura, T.; Sasaki, T.; Nagano, F.; Satoh, A.; Obaishi, H.; Nishioka, H.; Imamura, H.; Hotta, K.; Tanaka, K.; Nakanishi, H., et al. Isolation and characterization of a novel actin filament-binding protein from Saccharomyces cerevisiae. *Oncogene* 1998, 16, 121-130, doi:10.1038/sj.onc.1201487.

24. Akrap, N.; Seidel, T.; Barisas, B. G. Forster distances for fluorescence resonant energy transfer between mCherry and other visible fluorescent proteins. *Anal Biochem* 2010, 402, 105-106, doi:10.1016/j.ab.2010.03.026.

25. Loignon, M.; Perret, S.; Kelly, J.; Boulais, D.; Cass, B.; Bisson, L.; Afkhamizarreh, F.; Durocher, Y. Stable high volumetric production of glycosylated human recombinant IFNalpha2b in HEK293 cells. *BMC Biotechnol* 2008, 8, 65, doi:10.1186/1472-6750-8-65.

26. Jager, V.; Bussow, K.; Wagner, A.; Weber, S.; Hust, M.; Frenzel, A.; Schirrmann, T. High level transient production of recombinant antibodies and antibody fusion proteins in HEK293 cells. *BMC Biotechnol* 2013, 13, 52, doi:10.1186/1472-6750-13-52.

27. Bubb, M. R.; Spector, I.; Bershadsky, A. D.; Korn, E. D. Swinholide A is a microfilament disrupting marine toxin that stabilizes actin dimers and severs actin filaments. *J Biol Chem* 1995, 270, 3463-3466, doi:10.1074/jbc.270.8.3463.

28. Terry, D. R.; Spector, I.; Higa, T.; Bubb, M. R. Misakinolide A is a marine macrolide that caps but does not sever filamentous actin. *J Biol Chem* 1997, 272, 7841-7845, doi:10.1074/jbc.272.12.7841.

29. Rebbeck, R. T.; Singh, D. P.; Janicek, K. A.; Bers, D. M.; Thomas, D. D.; Launikonis, B. S.; Cornea, R. L. RyR1-targeted drug discovery pipeline integrating FRET-based high-throughput screening and human myofiber dynamic Ca(2+) assays. *Sci Rep* 2020, 10, 1791, doi:10.1038/s41598-020-58461-1.

30. Stroik, D. R.; Yuen, S. L.; Janicek, K. A.; Schaaf, T. M.; Li, J.; Ceholski, D. K.; Hajjar, R. J.; Cornea, R. L.; Thomas, D. D. Targeting protein-protein interactions for therapeutic discovery via FRET-based high-throughput screening in living cells. *Sci Rep* 2018, 8, 12560, doi:10.1038/s41598-018-29685-z.

31. Gruber, S. J.; Cornea, R. L.; Li, J.; Peterson, K. C.; Schaaf, T. M.; Gillispie, G. D.; Dahl, R.; Zsebo, K. M.; Robia, S. L.; Thomas, D. D. Discovery of enzyme modulators via high-throughput time-resolved FRET in living cells. *J Biomol Screen* 2014, 19, 215-222, doi:10.1177/1087057113510740.

32. Rebbeck, R. T.; Essawy, M. M.; Nitu, F. R.; Grant, B. D.; Gillispie, G. D.; Thomas, D. D.; Bers, D. M.; Cornea, R. L. High-Throughput Screens to Discover Small-Molecule 33. Lo, C. H.; Schaaf, T. M.; Grant, B. D.; Lim, C. K.; Bawaskar, P.; Aldrich, C. C.; Thomas, D. D.; Sachs, J. N. Noncompetitive inhibitors of TNFR1 probe conformational activation states. *Sci Signal* 2019, 12, doi:10.1126/sci signal.aav5637.
34. Lo, C. H.; Vunnam, N.; Lewis, A. K.; Chiu, T. L.; Brummel, B. E.; Schaaf, T. M.; Grant, B. D.; Bawaskar, P.; Thomas, D. D.; Sachs, J. N. An Innovative High-Throughput Screening Approach for Discovery of Small Molecules That Inhibit TNF Receptors. *SLAS Discov* 2017, 22, 950-961, doi:10.1177/2472555217706478.
35. Lo, C. H.; Lim, C. K.; Ding, Z.; Wickramasinghe, S. P.; Braun, A. R.; Ashe, K. H.; Rhoades, E.; Thomas, D. D.; Sachs, J. N. Targeting the ensemble of heterogeneous tau oligomers in cells: A novel small molecule screening platform for tauopathies. *Alzheimers Dement* 2019, 15, 1489-1502, doi:10.1016/j.jalz.2019.06.4954.
36. Hughes, J. P.; Rees, S.; Kalindjian, S. B.; Philpott, K. L. Principles of early drug discovery. *Br J Pharmacol* 2011, 162, 1239-1249, doi:10.1111/j.1476-5381.2010.01127.x.
37. Kumar, S.; Kain, V.; Sitasawad, S. L. Cardiotoxicity of calmidazolium chloride is attributed to calcium aggravation, oxidative and nitrosative stress, and apoptosis. *Free Radic Biol Med* 2009, 47, 699-709, doi:10.1016/j.freeradbiomed.2009.05.028.
38. Sorensen, M. G.; Karsdal, M. A.; Dziegiel, M. H.; Boutin, J. A.; Nosjean, O.; Henriksen, K. Screening of protein kinase inhibitors identifies PKC inhibitors as inhibitors of osteoclastic acid secretion and bone resorption. *BMC Musculoskelet Disord* 2010, 11, 250, doi:10.1186/1471-2474-11-250.
39. Hurley, J. D.; Akers, A. T.; Friedman, J. R.; Nolan, N. A.; Brown, K. C.; Dasgupta, P. Non-pungent long chain capsaicin-analogs arvanil and olvanil display better anti-invasive activity than capsaicin in human small cell lung cancers. *Cell Adh Migr* 2017, 11, 80-97, doi:10.1080/19336918.2016.1187368.
40. Shelley, M. D.; Hartley, L.; Groundwater, P. W.; Fish, R. G. Structure-activity studies on gossypol in tumor cell lines. *Anticancer Drugs* 2000, 11, 209-216, doi:10.1097/00001813-200003000-00009.
41. Ni, S.; Chen, X.; Yu, Q.; Xu, Y.; Hu, Z.; Zhang, J.; Zhang, W.; Li, B.; Yang, X.; Mao, F., et al. Discovery of candesartan cilexetic as a novel neddylation inhibitor for suppressing tumor growth. *Eur J Med Chem* 2020, 185, 111848, doi:10.1016/j.ejmech.2019.111848.
42. Irwin, J. J.; Duan, D.; Torosyan, H.; Doak, A. K.; Ziebart, K. T.; Sterling, T.; Tumanian, G.; Shoichet, B. K. An Aggregation Advisor for Ligand Discovery. *J Med Chem* 2015, 58, 7076-7087, doi:10.1021/acs.jmedchem.5b01105.
43. Ferreira, R. S.; Simeonov, A.; Jadhav, A.; Eidam, O.; Mott, B. T.; Keiser, M. J.; McKerrow, J. H.; Maloney, D. J.; Irwin, J. J.; Shoichet, B. K. Complementarity between a docking and a high-throughput screen in discovering new cruzain inhibitors. *J Med Chem* 2010, 53, 4891-4905, doi:10.1021/jm100488w.
44. Babaoglu, K.; Simeonov, A.; Irwin, J. J.; Nelson, M. E.; Feng, B.; Thomas, C. J.; Cancian, L.; Costi, M. P.; Maltby, D. A.; Jadhav, A., et al. Comprehensive mechanistic analysis of hits from high-throughput and docking screens against beta-lactamase. *J Med Chem* 2008, 51, 2502-2511, doi:10.1021/jm701500e.
45. Doak, A. K.; Wille, H.; Prusiner, S. B.; Shoichet, B. K. Colloid formation by drugs in simulated intestinal fluid. *J Med Chem* 2010, 53, 4259-4265, doi:10.1021/jm100254w.
46. Amin, A. D.; Rajan, S. S.; Groysman, M. J.; Pongtornpipat, P.; Schatz, J. H. Oncogene Overdose: Too Much of a Bad Thing for Oncogene-Addicted Cancer Cells. *Biomark Cancer* 2015, 7, 25-32, doi:10.4137/BIC.S29326.
47. Prochniewicz, E.; Chin, H. F.; Henn, A.; Hannemann, D. E.; Olivares, A. O.; Thomas, D. D.; De La Cruz, E. M. Myosin isoform determines the conformational dynamics and cooperativity of actin filaments in the strongly bound actomyosin complex. *J Mol Biol* 2010, 396, 501-509.
48. Prochniewicz, E.; Walseth, T. F.; Thomas, D. D. Structural dynamics of actin during active interaction with myosin: different effects of weakly and strongly bound myosin heads. *Biochemistry* 2004, 43, 10642-10652.
49. Nicita, F.; Nardella, M.; Bellacchio, E.; Alfieri, P.; Terrone, G.; Piccini, G.; Graziola, F.; Pignata, C.; Capuano, A.; Bertini, E., et al. Heterozygous missense variants of SPTBN2 are a frequent cause of congenital cerebellar ataxia. *Clin Genet* 2019, 96, 169-175, doi:10.1111/cge.13562.

Example 2

Figure 9:
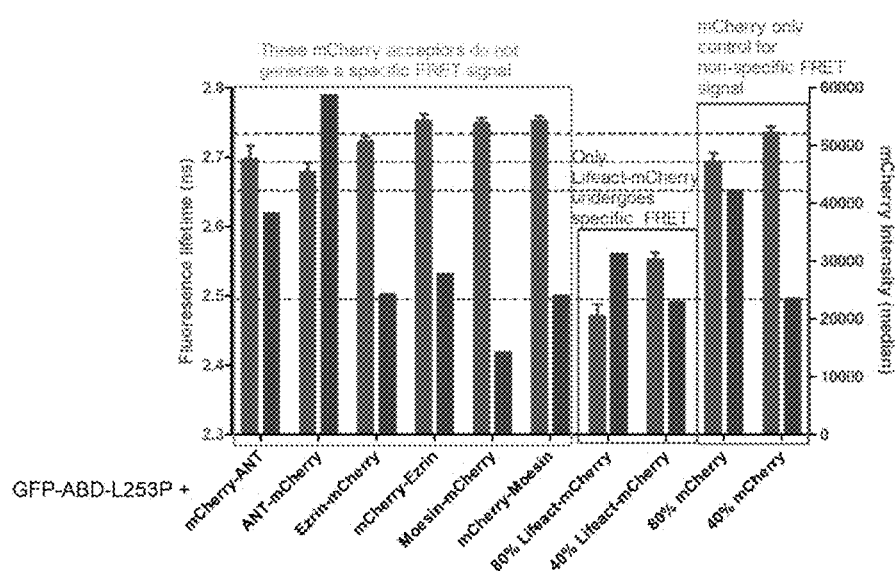
FIG. 9 shows GFP-ABD-L253P undergoes specific FRET with Lifeact-mCherry, but not other tested mCherry-actin-binding protein constructs. FRET acceptor constructs containing the actin-binding component, Lifeact, but not ANT, Ezrin or Moesin, decrease FLT (increases FRET) relative to the control FRET acceptor mCherry (no fusion to actin-binding protein).

Monitoring the Actin-Binding Activity of L253P Mutant β-III-Spectrin by FRET is Aided by Use of Lifeact-mCherry as the FRET Acceptor Example 1 reports the novel finding that binding of the GFP-tagged L253P β-III-spectrin actin-binding domain (GFP-ABD-L253P) to actin filaments can be detected in cells by FRET when the actin-binding peptide, Lifeact, fused to mCherry (Lifeact-mCherry) is used as the FRET acceptor. Here we tested whether the FRET assay requires Lifeact-mCherry as acceptor, or if other actin-binding proteins fused to mCherry can be substituted. Specifically we tested the alternative acceptor constructs consisting of the actin-binding proteins, myosin essential light chain N-terminal peptide (ANT), Ezrin or Moesin, fused to the N- or C-terminus to mCherry. As a control, we also tested the acceptor, mCherry, not fused to an actin-binding protein. In this assay, FRET is measured as a decrease in the fluorescence lifetime (FLT) of GFP-ABD-L253P. Of the tested acceptor constructs, Lifeact-mCherry (expressed at different levels by transfecting Lifeact-mCherry DNA at 40% or 80% of total DNA), decreased FLT of GFP-ABD-L253P relative to FLT of GFP-ABD-L253P observed using the control acceptor mCherry (expressed at 40% or 80%) (FIG. 9). Thus, monitoring the actin-binding activity of GFP-ABD-L253P cannot be accomplished using any actin-binding protein FRET acceptor construct. Instead the assay requires a select actin-binding proteins, such as Lifeact, as the acceptor construct.

Materials and Methods for Optimal FRET Assay

Expression constructs. FRET donor and acceptor constructs were generated using the plasmid expression vector, pcDNA3.1(+) (Invitrogen). The coding sequence for Lifeact-mCherry was PCR amplified from mCherry-Lifeact-7 (Addgene, plasmid #54491) using the oligonucleotides, AAAGGTACCATGGGCGTGGCCGACTTG and AAATCTAGATTACTTGTACAGCTCGTCCATGCC, and ligated into pcDNA3.1(+) using the restriction enzymes Kpn1 and Xba1, resulting in the construct pcDNA3.1-Lifeact-mCherry. To generate GFP-ABD expression constructs, a mEGFP DNA construct with flanking Kpn1 and EcoR1 restriction sites, was synthesized (Integrated DNA Technologies). The mEGFP sequence was subcloned into pcDNA3.1(+) using Kpn1 and EcoR1 restriction enzymes, resulting the in the construct, pcDNA3.1-GFP. DNA sequences encoding the wild-type or L253P human β-III-spectrin ABD (amino acids 1-284, NCBI reference sequence NP_008877.1) were PCR amplified from pE-SUMO-ABD-WT or -L253P (Avery, 2017 PMID: 29116080) using the oligonucleotides AAAGAATTCATGAGCAGCACGCTGT-CACCC and AAATCTAGACTACTTCATCTTG-GAGAAGTAATGGTAGTAAG, and inserted into pcDNA3.1-GFP using EcoR1 and Xba1 restriction enzymes. The resulting constructs, pcDNA3.1-GFP-ABD-WT and -L253P, along with pcDNA3.1-Lifeact-mCherry, were sequence verified. These constructs, along with the parental vector, pcDNA3.1(+), were prepared for transfection using NucleoBond Xtra Midi kit (Macherey-Nagel).

Cell culture and transfection. HEK293.2sus cells (ATTC CRL1573.3) were grown in DMEM (Thermo Fisher Scientific) containing 4.5 g/mL glucose and 0.862 g/L L-alanyl-glutamine and supplemented with 10% FBS and penicillin-streptomycin (complete media). Cells were maintained at 37° C. and 5% $CO_2$. For FRET assays, HEK293.2sus cells were dissociated with TrypLE (Thermo Fisher Scientific) and plated into a tissue culture-treated six-well microplate at a density of $0.5 \times 10^6$ cells per well. Twenty-four hours after plating, at 60-70% cell confluency, transient transfections were performed. One well in the 6-well microplate was transfected with GFP-ABD and Lifeact-mCherry, and a second, control well, was transfected with GFP-ABD only. Transfections were performed with Lipofectamine 3000 (Thermo Fisher Scientific) as described here: A transfection reaction for an individual well was prepared in a 1.5 mL microtube, by combining 500 ng GFP-ABD, 1000 ng Lifeact-mCherry (not included in control), and 1000 ng or 2000 ng pcDNA3.1(+), such that total DNA in the transfection reaction equaled 2500 ng. Opti-MEM I reduced serum media (Thermo Fisher Scientific) was added to microtubes containing DNAs for a total volume of 120 μL. Then, 5 μL P3000 (supplied in Lipofectamine 3000 transfection kit) was added to the transfection reaction mixture. Next, 125 μL of Opti-MEM, mixed with 5 μL Lipofeactime 3000, was added to the transfection reaction, for a total transfection reaction volume of 250 μL. The transfection reaction was mixed by pipetting and incubated for 5 min at room temperature. Next, the transfection reaction was pipetted into a single well of the 6-well microplate, and the microplate returned to the cell incubator for 24 h.

Harvesting cells. 24 h after transfection, cells were harvested from 6-well microplate by aspiration of media over cells, followed by brief wash performed by addition of 1 mL Dulbecco's Phosphate Buffered Saline (DBPS; Thermo Fisher Scientific) per well. Following aspiration of DPBS, cells were dissociated for 5 min in 250 μL TrypLE at 37° C. Then, cells were resuspended to 2.5 mL using complete media, and transferred to a 15 mL conical tube. Cells were further washed by pelleting at 100×g for 2 minutes, followed by aspiration of supernatant, and then resuspension of cell pellet in 5 mL DPBS. This wash step was repeated twice more. At the end of the final wash, cells were resuspended in ~1 mL DPBS for a cell density of $1 \times 10^6$/mL.

FRET Measurement. FRET in live cells was measured using a Fluorescence Lifetime (FLT) Plate Reader (FLTPR) (Fluorescence Innovations). Cells transfected with GFP-ABD and Lifeact-mCherry, or GFP-ABD only, were dispensed into a microplate containing up to 1536 wells. Fluorescence emission signals of the GFP-ABD were measured following pulsed excitation by a 473 nm laser. To quantify FLT, GFP-ABD emission signal waveforms were fit to a decay constant Tau (τ). FRET is calculated as the fractional decrease in FLT measured in cells co-expressing FRET donor, GFP-ABD, and FRET acceptor, Lifeact-mCherry ($\tau_{DA}$) relative to cells expressing GFP-ABD only ($\tau_D$), using the following equation:

$$FRET = 1 - \tau_{DA}/\tau_D$$

FRET between GFP-ABD-L253P and Lifeact-mCherry is highly specific

Figure 10:
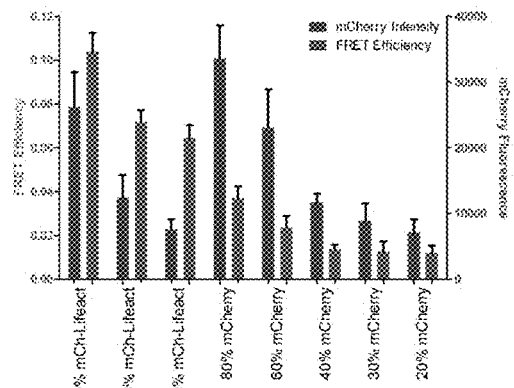
FIG. 10 shows FRET between GFP-ABD-L253P and Lifeact-mCherry is highly specific.
Figure 10:
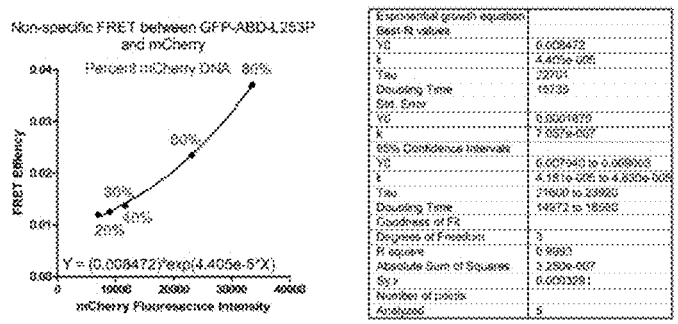
Figure 10:
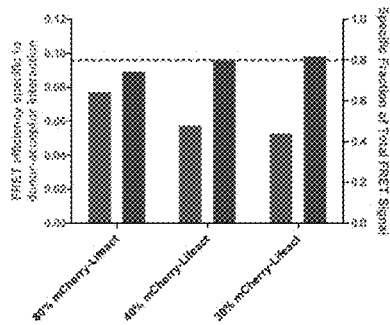

Example 1 reports that the FRET signal measured in cells expressing GFP-ABD-L253P together with Lifeact-mCherry has a "specific" and "non-specific" component. We define the specific component as the fraction of the FRET signal that is dependent on both the actin-binding component (ABD-L253P) of the donor construct (GFP-ABD-L253P) and the actin-binding component (Lifeact) of the acceptor construct (Lifeact-mCherry). In other words, non-specific FRET is the FRET signal measured in cells expressing GFP donor or mCherry acceptor that lacks actin-binding activity; for example: GFP-ABD-L253P together with mCherry (not fused to Lifeact). To improve the FRET assay for drug screening, we minimized the non-specific component to avoid measuring effects of compounds on the non-specific FRET signal. To accomplish this, we determined the relationship of FRET between GFP-ABD-L253P and Lifeact-mCherry or mCherry control, expressed at varying levels. At similar mCherry fluorescence intensities, the FRET efficiency is much higher in cells expressing GFP-ABD-L253P with Lifeact-mCherry relative to cells expressing GFP-ABD-L253P with mCherry control, FIG. 10A. To estimate non-specific FRET as a function of mCherry fluorescence intensity, non-linear regression was performed to fit an exponential curve to FRET and mCherry fluorescence data collected from cells expressing GFP-ABD-L253P and control mCherry, FIG. 10B. This relationship allowed estimation of the fraction of non-specific FRET for different Lifeact-mCherry expression levels. We determined that when GFP-ABD-L253P is co-expressed at 30-40% with Lifeact-mCherry, a FRET signal is produced that is >80% specific, FIG. 10C. This experiment shows that the assay is aided by specific DNA, transfection and cell incubation times in order to generate a FRET signal that specifically reports on the actin-binding activity of the mutant β-III-spectrin ABD.

FRET between GFP-ABD-L253P and Lifeact-mCherry is dependent on actin filaments

Figure 11:
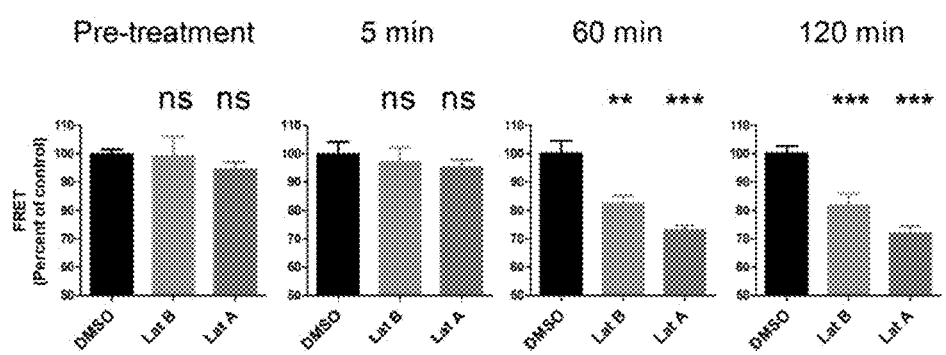
FIG. 11 shows FRET between GFP-ABD-L253P and Lifeact-mCherry is dependent on actin filaments. The decrease in FRET upon 60 min latrunculin A or B treatment supports the interpretation that the assay is monitoring the binding of the mutant ABD to actin filaments in living cells.

In Example 1 we reported molecular modeling which predicted that the L253P mutant β-III-spectrin ABD and the Lifeact peptide are docked at neighboring sites along the actin filament. This is significant as it is not been determined experimentally where the Lifeact peptide binds the actin-filament. This modeling further supports the interpretation that FRET between GFP-ABD-L253P and Lifeact-mCherry reflects the close proximity of these two proteins to each other due to their binding to neighboring sites on the same actin filament. To further validate this interpretation, we tested whether FRET efficiency is reduced following actin depolymerization using the drugs latrunculin A and latrunculin B. Significantly, we found that latrunculin A and B significantly reduce FRET between GFP-ABD-L253P and Lifeact-mCherry following 60 minutes of treatment, FIG. 11.

The FRET assay can be used to monitor, in real time, the actin binding of other mutant ABDs in cells.

Figure 12:
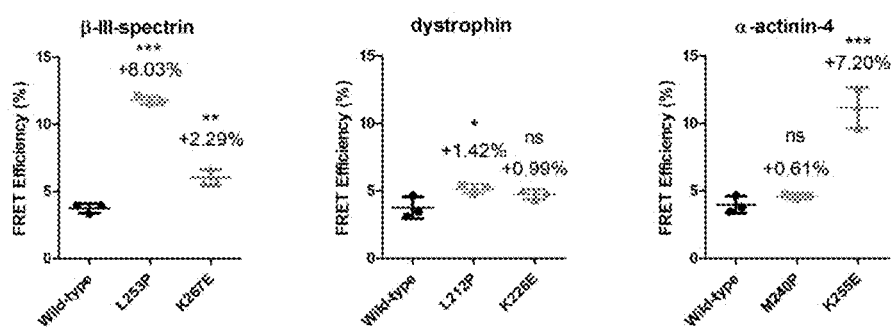
FIG. 12 shows Lifeact-mCherry can be used to monitor the actin-binding of activity of other mutant ABD proteins.
Figure 12:
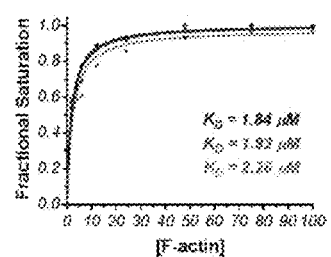

We tested whether Lifeact-mCherry could be used to monitor the actin-binding activity of other mutant ABD proteins. We generated additional donor constructs consisting of GFP fused to the ABD of the spectrin-related proteins dystrophin and α-actinin-4, and tested how introduction of the SCA5 L253P mutation into α-actinin-4 and dystrophin impacts actin binding of these proteins. We also tested how the α-actinin-4 disease mutation, K255E, and the equivalent mutation in β-III-spectrin and dystrophin, impact FRET. The differing FRET signals caused by these mutations is displayed in FIG. 12. Notably, K255E α-actinin-4, which binds actin with high affinity (Kd=46 nM; Weins, Proc Natl Acad Sci USA, 2007 104(41):16080-5), similar to L253P mutant β-III-spectrin (75 nM), produces a strong FRET signal, similar in magnitude to that observed for L253P β-III-spectrin, FIG. 12A. However, when the K255E mutation is introduced into β-III-spectrin (K267E), a much smaller increase in FRET is observed, suggesting this mutation does not increase actin binding as potently as it does in α-actinin, nor as strongly as the L253P mutation in β-III-spectrin. Interestingly, introduction of the L253P mutation into dystrophin (L212P), results in only a small, 1.4% increase in FRET. In vitro actin co-sedimentation assays, confirmed that L212P dystrophin binds actin with increased affinity (Kd=2 µM for L212P; wild-type=~45 µM; Singh et al., PloS one, 23 Oct. 2014, 9(10):e110439), FIG. 12B. These data indicate that the FRET assay has, at minimum, a sensitivity range of ~50 nM to 2 µM. Because the FRET assay can measure increases in FRET as low as ~0.5%, the dynamic range of the assay is likely broader. These data further demonstrate the ability of the FRET to resolve different levels of actin affinity. Significantly these data show that live cell FRET assays using Lifeact-mCherry can be developed for multiple human disease proteins containing mutations that increase actin binding.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for identifying a compound that alters fluorescence resonance energy transfer (FRET) of a protein comprising:
providing a genetically engineered cell comprising a first protein and a second protein,
wherein the first protein comprises a first heterologous domain that comprises a first probe, and the first protein comprises either a CH domain-containing actin-binding domain or a tandem-CH, actin-binding domain,
wherein the second protein comprises a second heterologous domain that comprises a second probe;
wherein each protein binds to an actin filament in the cell in a spatial proximity to result in detectable FRET between the first and second probes;
contacting the cell with a test compound to form a mixture; and
measuring the fluorescence lifetime of the first probe, the second probe, or the combination thereof.

2. The method of claim 1, wherein a difference between the fluorescence lifetime in the presence of the test compound and the fluorescence lifetime in the absence of the test compound indicates that the test compound alters the FRET of the target protein.

3. The method of claim 1 wherein the second protein is a fusion protein comprising a Lifeact protein and a red fluorescent protein.

4. The method of claim 1 wherein the Förster distance between the first probe and the second probe is at least 52 angstroms (Å).

5. The method of claim 1 wherein the first heterologous domain is located at the amino-terminal end of the first protein.

6. The method of claim 1 wherein the first heterologous domain is located at the carboxy-terminal end of the first protein.

7. The method of claim 1 wherein the first probe is a donor probe and the second probe is an acceptor probe.

8. The method of claim 1 wherein the measuring comprises capturing fluorescence lifetime waveforms emitted by the donor probe or the acceptor probe.

9. The method of claim 1 wherein the fluorescence lifetime of the donor probe is changed in the presence of the test compound.

10. The method of claim 9 wherein the fluorescence lifetime of the donor probe is reduced in the presence of the test compound.

11. The method of claim 1 wherein the fluorescence lifetime of the donor probe is unchanged in the presence of the test compound.

12. The method of claim 1 wherein the cell is exposed to an excitation light for no greater than 5 seconds.

13. The method of claim 1 wherein the first protein comprises a wild-type protein that further comprises the first heterologous domain.

14. The method of claim 1 wherein the first protein is a mutant actin-binding protein comprising a wild-type protein and at least one mutation.

15. The method of claim 1 wherein the at least one mutation is present in the tandem-CH, actin-binding domain or in the CH domain-containing actin-binding domain.

16. The method of claim 14 wherein the mutant actin-binding protein binds the actin filament with an affinity that is greater than the first protein in the absence of the at least one mutation.

17. The method of claim 1 wherein the first protein comprises a β-III-spectrin, the β-III-spectrin comprising a mutation that correlates with a disease in a human.

18. The method of claim 17 wherein the disease is spinocerebellar ataxia type 5.

19. The method of claim 17 wherein the mutation is L253P.

20. The method of claim 1 further comprising performing a counter screen, wherein the counter screen comprises:
   providing a genetically engineered cell comprising the first protein and the second probe;
   contacting the cell with the test compound to form a mixture; and
   measuring the fluorescence lifetime of the first probe, the second probe, or the combination thereof.

\* \* \* \* \*